(12) United States Patent
Merrill

(10) Patent No.: US 12,312,286 B1
(45) Date of Patent: *May 27, 2025

(54) SYSTEMS AND/OR METHODS FOR PRODUCING SYNTHETIC HYDROCARBONS FROM BIOMASS

(71) Applicant: Matthew D. Merrill, Charlottesville, VA (US)

(72) Inventor: Matthew D. Merrill, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/418,403

(22) Filed: Jan. 22, 2024

Related U.S. Application Data

(63) Continuation of application No. 18/220,409, filed on Jul. 11, 2023, now Pat. No. 11,912,637, which is a continuation of application No. 17/959,478, filed on Oct. 4, 2022, now Pat. No. 11,767,274.

(51) Int. Cl.
| | | |
|---|---|---|
| C07J 3/00 | (2006.01) |
| C07C 1/04 | (2006.01) |
| C07C 1/12 | (2006.01) |
| C10J 3/00 | (2006.01) |
| C25B 9/00 | (2021.01) |
| C25B 9/65 | (2021.01) |
| C25B 9/67 | (2021.01) |

(52) U.S. Cl.
CPC .......... *C07C 1/0485* (2013.01); *C07C 1/0475* (2013.01); *C07C 1/0495* (2013.01); *C07C 1/12* (2013.01); *C10J 3/00* (2013.01); *C10J 2300/0906* (2013.01); *C10J 2300/0916* (2013.01); *C10J 2300/1684* (2013.01)

(58) Field of Classification Search
None
See application file for complete search history.

(56) References Cited

U.S. PATENT DOCUMENTS

| | | | | |
|---|---|---|---|---|
| 2022/0136119 A1* | 5/2022 | Flanders | ............ | B01D 53/1493 435/71.1 |
| 2023/0072869 A1* | 3/2023 | Bitting | .................... | C10K 3/008 |
| 2023/0116183 A1* | 4/2023 | Bitting | ........................ | C10J 3/62 585/241 |
| 2023/0117658 A1* | 4/2023 | Bitting | ................... | C10G 1/002 208/14 |

* cited by examiner

*Primary Examiner* — Tam M Nguyen
(74) *Attorney, Agent, or Firm* — Michael Haynes PLC; Michael N. Haynes

(57) ABSTRACT

Certain exemplary embodiments can provide a system, machine, device, manufacture, circuit, composition of matter, and/or user interface adapted for and/or resulting from, and/or a method and/or machine-readable medium comprising machine-implementable instructions for, activities that can include and/or relate to, converting biomass to synthetic hydrocarbons using a biomass thermal decomposer and/or a hydrocarbon synthesizer.

15 Claims, 5 Drawing Sheets

SYSTEMS AND/OR METHODS FOR PRODUCING SYNTHETIC HYDROCARBONS FROM BIOMASS

BRIEF DESCRIPTION OF THE DRAWINGS

A wide variety of potential, feasible, and/or useful embodiments will be more readily understood through the herein-provided, non-limiting, non-exhaustive description of certain exemplary embodiments, with reference to the accompanying exemplary drawings in which.

DESCRIPTION

Figure 1:
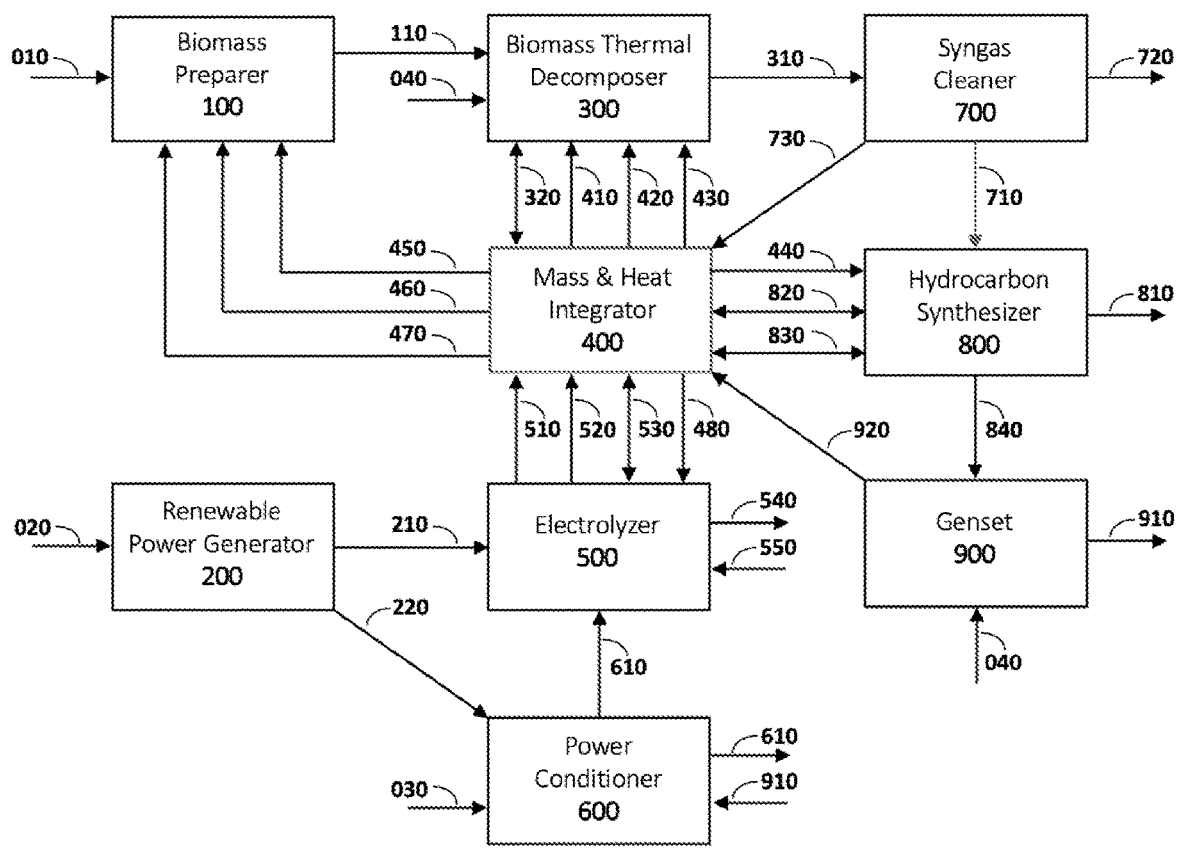
FIG. 1 is a block diagram of an exemplary embodiment of a system.

Certain embodiments can provide systems and/or methods for renewably producing synthetic hydrogen fuel, synthetic natural gas, synthetic liquifiable hydrocarbon fuels, and/or other synthetic hydrocarbons from biomass, low-carbon energy resources, and/or variable renewable energy through integrated mass and energy balance processes, components, and/or subsystems. Electrical power from solar, wind, hydrokinetic, and/or other energy sources can be stored via the electrolysis of water as separated hydrogen and oxygen gases. The separate hydrogen and oxygen gases can be supplied to biomass gasification and/or hydrocarbon synthesis processes, components, and/or subsystems to improve the yield and/or performance of the overall system. Mass and/or heat integration processes, components, and/or subsystems, such as a compressed gas storage, electrical power storage, water storage, heat transfer fluid storage, heat exchange, and/or conveyance processes, components, and/or subsystems, can efficiently store energy, heat, and/or mass on temporary basis, and/or supply the energy, heat, and/or mass under more steady state conditions to the energy conversion and/or fuel synthesis processes. Certain material products and/or byproducts of the biomass conversion, hydrocarbon synthesis, and/or electrolysis processes can be stored in the mass and/or heat integrator for later selective recycling as "recycle mass". Certain exemplary embodiments can apply renewable energy to convert biomass to syngas to synthetic hydrocarbons (e.g., synthetic hydrocarbon fuels such as diesel and gasoline), whereby heat and/or mass can be stored and/or delivered to balance and control the overall process.

Certain embodiments can provide systems, machines, and/or methods for producing synthetic hydrocarbons from biomass and/or renewable energy. A mass and energy integrator (or mass and heat integrator) can function to support greater variation in energy and/or biomass supply rates, temporarily store mass and/or energy, supply the mass and/or energy under more steady state conditions to the biomass thermal decomposition and/or hydrocarbon synthesis processes, enable advanced process control and automation capabilities, and/or improve the technical and/or economic performance of the overall system. Modularization and/or more independent operation of the processes for synthesizing hydrocarbons from biomass and/or renewable electrical power can improve the performance of the overall system at smaller scales and/or variable methods of use. Exemplary embodiments can comprise the primary forms of energy storage that include, but are not limited to, storage of prepared biomass, storage of electrical power, and storage of hydrogen ($H_2$) gas and/or other chemical intermediates.

Certain embodiments can use biomass and/or electrical power obtained from renewable and/or low-carbon resources (e.g., solar, wind, hydro, geothermal, nuclear, and/or other sources) to produce hydrogen, synthetic hydrocarbons, carbon dioxide ($CO_2$), and/or electricity. The synthetic hydrocarbons can comprise fuels, chemicals, solvents, oils, and/or waxes. For example, synthetic hydrocarbons can comprise methane, ethane, liquifiable petroleum gases (e.g., propane, butane, propylene), gasoline, jet fuel, diesel, oils, methanol, ethanol, and/or other hydrocarbons and/or other oxygenated hydrocarbons.

Certain exemplary embodiments can meet the interdependent needs of addressing climate change and cost-effectively producing renewable synthetic fuels. Certain exemplary embodiments can capture energy and/or carbon from biomass which can help mitigate and/or reverse the adverse effects of climate changes resulting from anthropogenic emissions of carbon dioxide ($CO_2$) and other greenhouse gases. Certain exemplary embodiments can provide a drop-in replacement of fossil fuels with synthetic hydrocarbon fuels and/or can have the potential for rapid and/or high impacts on $CO_2$ emissions by minimizing the need to alter the infrastructure that can use these fuels.

Via certain exemplary embodiments, significant quantities of net $CO_2$ emission reductions can be achieved by utilizing synthesized hydrocarbon fuels produced from biomass instead of utilizing fossil fuels extracted from the ground. The greatest impacts on net $CO_2$ emissions can be achieved when biomass that would otherwise go unused is instead utilized by certain exemplary embodiments to produce synthetic hydrocarbons such as synthetic hydrocarbon fuels. For example, in certain exemplary embodiments, agricultural crop residues left in the field, forestry residues, compost, and/or organic landfill materials can undergo decomposition to release wasted energy and/or carbon. Any carbon-based material that can decompose to synthesis gas ("syngas") at temperatures below 1,200 degrees Celsius, including but not limited to energy crops, coal, petroleum, fiber, and plastics can be used in certain embodiments. Fuels, such as hydrogen, synthetic natural gas and liquifiable synthetic hydrocarbon fuels, can be produced from this energy and carbon in a "biomass to gas" and/or "biomass to liquid" approach. Biomass used by certain exemplary embodiments might contain only enough energy to convert about 30-50% of the carbon in the biomass to fuel while the remaining carbon would be released into the atmosphere as $CO_2$ if not sequestered or used by such embodiments. In certain exemplary embodiments, additional energy from a renewable resource, such as solar, wind, hydrokinetic, and/or other resource, can be used to generate electrical power that can be added to the hydrocarbon synthesis process to convert greater fractions of the biomass to one or more synthetic hydrocarbons. Electrical power from nuclear, natural gas, and/or other resources also can be utilized in certain exemplary embodiments.

Certain exemplary embodiments can utilize gasification to apply heat to thermally decompose biomass into synthesis gas, which primarily can be a combination of carbon monoxide (CO) and hydrogen ($H_2$), but also can include significant fractions of carbon dioxide ($CO_2$) and/or methane ($CH_4$). In certain exemplary embodiments, gasification also can produce biomass thermal decomposition byproducts (i.e., gasification byproducts), such as liquids, which will be referred to as "tar" herein, and/or carbonized solids, which will be referred to as "biochar" herein. For simplicity, the use of gasification will herein encompass the related processes of pyrolysis, liquefaction, partial combustion, and other processes associated with thermal decomposition of biomass. In certain exemplary embodiments, the relative quantities of syngas, biochar, and tar can be somewhat dependent upon the type of gasification and/or corresponding process conditions. Via certain exemplary embodiments, using syngas to create synthetic hydrocarbons (e.g., synthetic fuels such as methane, diesel, and/or gasoline) can be favored by process conditions that produce relatively greater quantities of syngas than tar and char. Biomass thermal decomposition byproducts (of biomass decomposition (syngas production)), such as biochar, tar, volatile nitrogen, volatile sulfur, and/or other potential contaminants, can be removed from the syngas prior to the catalytic conversion of the syngas to synthetic fuels and/or other synthetic hydrocarbons. In certain exemplary embodiments, biomass thermal decomposition byproducts (from the gasified biomass) that can serve as nutrients, such as non-volatilized nitrogen, sulfur, phosphorous, potassium, calcium, magnesium, and/or transition metal compounds, can be retained in the biochar. The biochar can be a nutrient-rich agricultural crop fertilizer that can enhance the retention of nutrients, organic carbon, and/or water ($H_2O$) in soils.

Certain exemplary embodiments can utilize and/or generate hydrocarbon fuels, which can be forms of carbon that have been reduced to low oxidation states. The reduction of carbon can decrease the oxidation state of carbon by concentrating electrons on the carbon atoms. Via certain exemplary embodiments, hydrocarbon fuels with more reduced carbon can release more energy when the fuel is oxidized with oxygen ($O_2$) to the highest carbon oxidation state of carbon dioxide ($CO_2$). The degree that carbon has been reduced can be described in terms of functional equivalents of hydrogen ($H_2$) that have been added to $CO_2$. For example, in certain exemplary embodiments, the addition of $H^2$ to $CO_2$ can produce CO according to the reverse water gas shift reaction of equation (1). The addition of 4 units of $H^2$ to $CO_2$ can produce methane ($CH_4$) according to the methanation reaction of equation (2). Via certain exemplary embodiments, methane can be upgraded to natural gas through purification and compression to meet local natural gas pipeline standards. In certain exemplary embodiments, methane can be synthesized by reducing CO with 3 units of $H^2$ according to reaction of equation (3). Certain exemplary embodiments can synthesize liquifiable synthesized such as propane, gasoline, diesel, jet fuels, methanol, ethanol, ethers, and/or other compositions that can be approximated as $(CH_2)_n$, where n is the number of carbon atoms in the synthesized hydrocarbon molecules. With certain exemplary embodiments, a distribution of liquifiable synthesized hydrocarbon fuels can be synthesized from syngas through the Fischer-Tropsch process represented by the reaction of equation (4). Via certain exemplary embodiments, synthesized hydrocarbon fuels can be synthesized through the methanol ($CH_3OH$) route according to the reactions of equations (5)-(6). In certain exemplary embodiments, the fuel synthesizer can incorporate catalysts capable of selectively performing relevant fuel synthesis reactions that can include, e.g., various combinations of equations (1)-(6). With certain exemplary embodiments, the gasification of biomass can produce a syngas with a relatively low effective composition of $1H_2$ per 1 CO to $2H_2$ per 1 CO to $3H_2$ per 1 CO, which can be attained when synthesizing natural gas. In certain exemplary embodiments, additional $H_2$ can be added to the synthesis gas to increase the quantity of synthesized hydrocarbons and/or synthesized hydrocarbon fuel that is produced from the gasified biomass and/or to optimize the overall fuel synthesis process. Natural gas or other carbon-rich compounds also can be fed to the gasifier along with the biomass to increase the $H_2$ to CO ratio in the resulting syngas. In certain exemplary embodiments, the water gas shift reaction, which is the reverse of equation (1), can be applied to manage the $H_2$ per CO ratio. For certain exemplary embodiments, the output of the hydrocarbon synthesis (e.g., Fischer-Tropsch, cracking, etc.) process can include gases, such as butane ($C_4H_{10}$), propane ($C_3H_8$), ethane ($C_2H_6$), $CH_4$, $H_2$, CO, and/or $CO_2$, that can be stored and/or selectively recycled to various stages of the gasification and/or hydrocarbon synthesis processes. In certain exemplary embodiments, the hydrocarbon synthesis processes can produce oxygenated hydrocarbons, such as alcohols, carboxylic acids, ethers, ketones, or other oxygenates. In certain exemplary embodiments, the hydrocarbon synthesis processes can produce water, which can be stored and/or recycled for use in gasification, water electrolysis, and/or other processes relevant to the overall system. If certain synthetic hydrocarbons, such as propane, butane, alcohols, carboxylic acids, ethers, or other liquifiable products of fuel synthesis are undesirable for a given application, then via certain exemplary embodiments, any of those products can be stored and/or selectively recycled through the gasifier and/or oligomerized to larger hydrocarbons. In certain exemplary embodiments, if certain synthetic hydrocarbons are produced, such as waxes or other products of hydrocarbon synthesis whose molecular weights are too large to be desirable for a given application, then those synthetic hydrocarbons can be cracked into smaller, potentially more valuable products in an additional refining step. In certain exemplary embodiments, waxes and/or other synthetic hydrocarbons with large molecular weights can be stored and/or selectively recycled through the gasifier, which can help to avoid additional equipment costs and/or process complexity.

$$CO_2 + H_2 \Rightarrow CO + H_2O \tag{1}$$

$$CO_2 + 4H_2 \Rightarrow CH_4 + 2H_2O \tag{2}$$

$$CO + 3H_2 \Rightarrow CH_4 + H_2O \tag{3}$$

$$n\,CO + 2nH_2 \Rightarrow (CH_2)_n + nH_2O \tag{4}$$

$$CO + 2H_2 \Rightarrow CH_3OH \tag{5}$$

$$n\,CH_3OH \Rightarrow (CH_2)_n + nH_2O \tag{6}$$

In certain exemplary embodiments, the heat used for gasification can be generated by releasing a fraction of the chemical energy of the biomass through one or more exothermic chemical reactions. For example, the partial oxidation of biomass can be simply represented as graphitic carbon (C) with oxygen ($O_2$) with the exothermic reaction of equation (7). Since $O_2$ follows nitrogen ($N_2$) as the second largest component of air, this $O_2$ can be introduced into the gasification process by injecting air as a gasifying agent into the gasifier. In certain exemplary embodiments, purified $O_2$ can be injected as a gasifying agent into the gasifier to thermally decompose the biomass into syngas with the heat released by the reaction of equation (7). The overall system can be designed and/or operated to justify the equipment and/or energy costs of producing purified $O_2$ for injection into the gasifier. The injection of steam ($H_2O$) and/or $CO_2$ into the gasifier as gasifying agents can generate heat for the biomass gasification process through the exothermic reactions of equations (8) and (9), respectively. The gasification process can be designed to generate heat through the reactions of equations (8) and (9) because they can retain more chemical energy in the syngas than the reaction of equation (5) alone. Greater quantities of chemical energy in the syngas can enable higher yields of synthetic hydrocarbons, such as synthetic hydrocarbon fuel products.

$$C + \tfrac{1}{2} O_2 \Rightarrow CO \quad (7)$$

$$C + H_2O \Rightarrow CO + H_2 \quad (8)$$

$$C + CO_2 \Rightarrow 2\,CO \quad (9)$$

Separated $H_2$ and $O_2$ can be produced by the electrolysis of water with the input of electrical power through the reaction of equation (10). Water electrolysis can be performed with proton exchange membrane (PEM), alkaline, solid oxide, and/or other electrolytic cells. The coproduction of separated $H_2$ and $O_2$ through water electrolysis can simultaneously enable adding $H_2$ to increase the yield of the synthesis process and adding pure $O_2$ to the gasification process. The $H_2$ from electrolysis can be added in the gasification stage and/or the hydrocarbon synthesis stage. Syngas and/or other gaseous products of the fuel synthesis stage that are rich in $H_2$, CO, and/or hydrocarbons can be stored and/or selectively recycled to enhance the gasification stage and/or the hydrocarbon synthesis stage. Certain exemplary embodiments can incorporate high temperature water (>200° C.) electrolysis using technology based on solid oxide electrolysis, where the heat required for performing electrolysis at high temperatures is supplied from the gasifier. In certain exemplary embodiments, the water electrolysis process can be performed under relatively non-steady state rates in response to potentially intermittent character of renewable energy supply.

$$2H_2O \Rightarrow 2H_2 + O_2 \quad (10)$$

Mass and/or energy balancing can be incorporated into the overall process system design and/or operations. The capacities of the biomass storage, biomass processing, electrical energy storage, water electrolysis, gasifier, syngas purification, hydrocarbon synthesis, gas compression, and/or other processes can be balanced to maximize product yields and/or minimize equipment costs. For certain exemplary embodiments, the costs of equipment procurement, installation, operation, and/or maintenance can be approximately proportional to equipment size. Therefore, equipment size and/or related costs can be minimized by approaching a target steady state, high-capacity throughput for gasifier, electrolysis, and/or hydrocarbon synthesis subsystems, components, and/or processes. In certain exemplary embodiments, the gasification, electrolysis, and/or hydrocarbon synthesis subsystems, components, and/or processes can be operated near a target rating of steady state, high-capacity throughput to support safe and reliable process control and/or high product yields of synthetic hydrocarbons. Certain exemplary embodiments can switch from the synthesis of synthetic hydrocarbons (e.g., synthetic hydrocarbon fuels) from to generating electrical power directly from the syngas via a genset (i.e., a mated combination of a syngas-fueled combustion engine and an electrical power generator, where the operating engine drives the generator). Certain exemplary embodiments can generate electricity from biomass gasification, for example, by diverting the resulting syngas away from the synthesizer and instead to a combustion engine, which can be operated as a separate system located at the same site.

Certain exemplary embodiments can be designed and/or operated to use both pure $O_2$ gas as a gasifying agent by the gasifier and pure $H_2$ gas as a reducing agent that increases the fuel synthesis yields. Certain exemplary embodiments can produce enough pure $O_2$ gas from water electrolysis to operate the gasifier near full capacity without supplying substantial quantities of air as a gasifying agent to the gasifier. The biomass gasifier can be predominantly supplied with pure $O_2$ gas produced by water electrolysis at levels near the minimum operational requirement without a substantial supply of air to the gasifier. In certain exemplary embodiments, predominantly operating the gasifier with pure $O_2$ gas and without air can be affected by supplying the gasifier with recycle gas streams from the hydrocarbon synthesis processes that are rich in $H_2$, CO, and/or other fuel gases, recycle streams that include liquid and/or solid byproducts of fuel synthesis (i.e., synthesis byproducts), and/or an external source of methane-rich gas. The point at which the water electrolysis system is producing enough pure $O_2$ gas to meet the minimum requirement for significantly air-free operation of the gasifier is herein referred to as the $O_2$ balance condition. Certain exemplary embodiments can be designed and/or operated on average near or above the $O_2$ balance condition. The $O_2$ balance condition can be regarded as a general average or conceptual condition instead of an exact point because the exact $O_2$ balance point might subject to relatively small changes due to weather patterns, system maintenance, biomass composition, and/or other relevant factors. The $N_2$ gas concentration in the syngas can be below 20 volume percent, such as below 10 volume percent, when operating near or above the $O_2$ balance condition. The overall system can be designed and/or used so that the renewable energy generated by the system can be applied to water electrolysis for supplying enough $O_2$ gas to at least meet the $O_2$ balance condition. Additional electrical power from external sources, such as the electric utility grid, can be applied to electrically power water electrolysis and/or equipment other than the water electrolysis subsystem. Certain exemplary embodiments can operate without any non-intermittent electrical power to produce $O_2$ gas through water electrolysis. Certain exemplary embodiments can be designed and/or operated substantially below the $O_2$ balance condition, whereby the gasifier demand for significantly air-free operation is substantially not met by $O_2$ gas supplied by water electrolysis. Certain exemplary embodiments can be designed and/or operated below the $O_2$ balance condition by using air instead of purified $O_2$ due to effects that include, but are not limited to, the system startup and shutdown cycles, lack of electrical power supply for water electrolysis, and enabling a greater capacity for biomass gasification.

Certain exemplary embodiments can produce $O_2$ gas through water electrolysis in excess of the $O_2$ balance condition by increasing the scale of the renewable electrical power supply and/or supplying the additional electrical power from external sources (i.e., the utility grid). Although designing and/or operating the overall system substantially above the $O_2$ balance condition might increase the synthetic hydrocarbon yields by supplying additional $H_2$ gas to the hydrocarbon synthesis processes, the overall system might not benefit from the excess $O_2$ gas unless the excess $O_2$ gas is used and/or sold for alternative applications.

The carbon balance condition can occur when the water electrolysis system is producing enough pure $H_2$ gas to meet the minimum requirement for converting approximately all of the relevant CO or $CO+CO_2$ produced by the overall system to synthetic hydrocarbons. The carbon balance condition will be regarded as a general average and/or conceptual condition instead of an exact point because the exact carbon balance point might be subject to relatively small changes due to weather patterns, system maintenance, biomass composition, and/or other relevant factors. The carbon balance condition for certain exemplary embodiments focused on producing renewable natural gas can include up to 20 mol % excess $H_2$ gas in the synthetic natural gas composition. Certain exemplary embodiments can generally operate between the $O_2$ balance condition and the carbon balance condition. $CO_2$ or CO need not be supplied from feed sources other than the biomass. Additional $CO_2$ and/or CO can be produced internally by increasing the scale of biomass gasification. Certain exemplary embodiments can separate $CO_2$ from other gaseous products of biomass gasification, yet not necessarily require sequestration and/or use of this separated $CO_2$.

In certain exemplary embodiments, the supply of mass between the water electrolyzer, gasifier, and/or hydrocarbon synthesizer can control the mass balance, energy balance, and/or processing rates of one or more processes, components, and/or subsystems. $H_2$ gas produced by water electrolysis can be supplied to the hydrocarbon synthesizer. $O_2$ gas produced by water electrolysis can be supplied to the gasifier. Fuel gas, such as gaseous streams from the hydrocarbon synthesizer that are rich in $CO_2$, $H_2O$, CO, and/or synthetic hydrocarbons, can be selectively stored, selectively recycled to the gasifier, and/or selectively supplied to the genset for production of electrical power and/or heat. In certain exemplary embodiments, the relative rates of fuel gas recycling to the gasifier and/or the relative rate of supply of fuel gas to the genset can be used to control the concentrations of $N_2$ and/or $CO_2$ in the gasifier and/or hydrocarbon synthesis streams. In certain exemplary embodiments, storing and/or selectively supplying $H_2O$ gas might include storing $H_2O$ in the liquid state. Streams of liquid and/or solid hydrocarbon synthesis byproducts can be selectively stored and/or selectively recycled to the gasifier. Any of these streams can undergo temporary storage to allow one or more processes, components, and/or subsystems to be scaled and/or operated to improve hydrocarbon synthesis production rates and/or costs.

Electrical power supplied from solar, wind, hydrokinetic, or other renewable energy sources can be variable and/or intermittent in character due to diurnal, weather, seasonal, and/or other effects. In certain exemplary embodiments, solar panels can produce peaks in electrical power production during approximately 4 to approximately 6 hours near the middle of the day, can produce intermittent electrical power due to cloud patterns, and/or be inactive overnight. In certain exemplary embodiments, the biomass gasification and/or hydrocarbon synthesis processes, components, and/or subsystems can be used at or close to steady conditions at rates and/or capacities that approximate their target performance specifications. Certain exemplary embodiments can scale the renewable electrical power supply, water electrolysis, and/or gas storage processes, components, and/or subsystems to produce and/or store enough $O_2$ gas, $H_2$ gas, and recycled materials to enable the gasifier and/or hydrocarbon synthesizer to typically operate at or close to steady conditions at rates and/or capacities that approximate their nameplate and/or target performance specifications. In certain exemplary embodiments, the mass storage and/or supply unit (e.g., mass and heat integrator) can be designed and/or used to selectively load-level the gasifier and/or hydrocarbon synthesis processes, components, and/or subsystems. The capacities for $H_2$ gas and/or $O_2$ gas storage can be scaled to at least 1 hour and even to the equivalent of approximately 0.3 to approximately 3 days of operating requirements for the gasifier and/or fuel synthesis. Any recycle material can be selectively stored, such as via the mass and heat integrator, at a scale that can supply the gasifier for at least 1 hour of operation and even to the equivalent of approximately 0.3 to approximately 3 days of gasifier operation. Such selective storage can enable the production and/or storage of $H_2$ and $O_2$ gases while the gasifier is offline. Certain exemplary embodiments can be designed and/or used so that on average the gasifier is operating near peak throughput for greater than 9 hours per day on average throughout the year for an equivalent of approximately 35% to approximately 100% of annual capacity.

In certain exemplary embodiments, the $H_2$ gas can be produced at pressures of approximately 3 to approximately 100 bar through water electrolysis and/or stored under pressures of approximately 3 to approximately 800 bar at scales of approximately 1,000 to approximately 100,000 $Nm^3$. In certain exemplary embodiments, a significant time delay that can exist between recycle gas production by the downstream hydrocarbon synthesis process and recycle gas consumption by the upstream gasifier during a startup process can be compensated with a reserve of stored recycle materials. In certain exemplary embodiments, such stored reserves of recycle materials can be selectively applied with combustion to dry, densify, and/or preheat the biomass in preparation for gasification.

In certain exemplary embodiments, the storage system (which can be and/or include, e.g., the heat and mass integrator) can couple the intermittent and/or variable renewable energy supply with steady state gasification and/or hydrocarbon synthesis by incorporating thermal energy storage. In certain exemplary embodiments, a high temperature (>200° C.) water electrolysis technology, such as solid oxide electrolysis, can be incorporated into the overall system such that the electrolysis heat requirements are supplied from heat generated by the gasifier. In certain exemplary embodiments, the heat generated by the gasifier can be temporarily stored to enable the high temperature electrolysis system to operate more independently from the gasifier. The storage system can include a thermal energy storage system based on a molten salt, liquid metal, water, steam, air, oil, or other thermal transfer fluid plus fluid reservoir.

In certain exemplary embodiments, electrical power can be used to separate water into $H_2$ gas and $O_2$ gas through water electrolysis. Storage of $H_2$ and $O_2$ gases can allow for load-leveling the gasifier and/or hydrocarbon synthesis processes over the scale of hours to days. In certain exemplary embodiments, batteries, capacitors, compressed air energy storage, and/or other technologies that store electrical power also can be used as a complimentary approach of energy storage. In certain exemplary embodiments, the complimentary approach to electrical power storage can be used to peak shave the supply of renewable electrical power to the water electrolysis system on the scale of minutes to hours, reduce the size of the water electrolysis system, and/or protect the water electrolysis system from rapid decreases and/or increases in electrical power supply caused by weather. In certain exemplary embodiments, the water electrolysis system size can be significantly reduced and/or the capacity increased by up to 60% through peak shaving, which can involve temporarily storing a fraction of the electrical power produced during peak output and then applying the stored electrical power towards water electrolysis during low electrical power output by the solar panels and/or other renewable electrical power source. Peak shaving therefore enables the overall system to operate a smaller water electrolysis system with electrical power that is supplied more closely to target ratings.

The biomass can be conditioned for use with methods that can be functionally analogous to the conditioning of power for use. For example, certain exemplary embodiments can include a biomass preparation process to dry, densify, and/or store the biomass for thermal decomposition. The storage of biomass in the dried, densified condition can preserve the quality of the biomass through time, decreases the space and/or equipment required to store the biomass, and/or increase the effective annual capacity of biomass thermal decomposition. In certain exemplary embodiments, the scale of hydrocarbon synthesis facilities for producing synthetic hydrocarbons, such as synthetic hydrocarbon fuel, synthetic natural gas, and/or liquified synthetic hydrocarbons can correspond to approximately 0.5 to approximately 30 MW of electrical power input and/or approximately 500 to approximately 30,000 tonnes of biomass per year.

The relative scale of an applied throughput of a process, component, and/or subsystems can be described as a product of the nominal power rating and an average operating capacity. For example, a gasifier with a nominal thermochemical power throughput rating of 1.25 MW and an annual capacity of 80% due to maintenance has an applied throughput of 1.0 MW. A water electrolysis system with a nominal electrical throughput of 2.0 MW and an average capacity of 25% has an applied throughput of 0.5 MW. In certain exemplary embodiments, the applied energy throughput of the gasification component can be about 2 times larger than the applied throughputs of the renewable electrical power source and water electrolysis components for systems operated near the $O_2$ balance condition according to the average applied throughout ratio relationship of equation (11). In certain exemplary embodiments, the relative scale of the applied throughputs of the renewable electrical power source and water electrolysis components can increase by approximately 2 to approximately 3 times for systems operated near the carbon balance condition, depending on biomass input composition, synthetic hydrocarbon product composition, and/or other process conditions. In certain exemplary embodiments, the average applied throughput imposed by the carbon balance condition can be described by the ratio relationship of equation (12). Certain exemplary embodiments can be designed and/or used with $H_2$ gas, $O_2$ gas, and/or recycle gas storage capabilities sufficient for applied, average operation between the ratio relationships of equations (11) and (12).

$$1 \text{ MW of gasifier} > 0.3 \text{ MW of water electrolysis and} > 0.0 \text{ MW of renewable electrical power} \quad (11)$$

$$1 \text{ MW of gasifier} < 2.5 \text{ MW of water electrolysis and} < 5 \text{ MW of renewable electrical power} \quad (12)$$

Certain exemplary embodiments can include at least one apparatus, machine, system, manufacture, composition of matter, and/or method configured for applying electrical power to convert biomass to synthetic hydrocarbons. FIG. 1 is a block diagram of an exemplary embodiment of a system 1000, for which a key can be found below.

| | |
|---|---|
| 010 | Biomass |
| 020 | Renewable energy |
| 030 | Power from external source |
| 040 | Air |
| 100 | Biomass Preparer |
| 110 | Prepared biomass |
| 200 | Renewable Power Generator |
| 210 | Electrical power for water electrolysis |
| 220 | Electrical power for storage |
| 300 | Biomass Thermal Decomposer |
| 310 | Thermally decomposed biomass |
| 320 | Heat byproduct of thermal decomposition |
| 400 | Mass & Heat Integrator |
| 410 | $H_2$ gas to biomass thermal decomposer |
| 420 | Electrolyzer $O_2$ gas to biomass thermal decomposition |
| 430 | Recycle mass to biomass thermal decomposition |
| 440 | Electrolyzer $H_2$ gas to hydrocarbon synthesis |
| 450 | Heat for biomass preparation |
| 460 | Recycle mass to biomass preparation |
| 470 | Electrolyzer $O_2$ gas to biomass preparation |
| 480 | Water recycle to supply water electrolysis |
| 500 | Electrolyzer |
| 510 | Electrolyzer $H_2$ gas |
| 520 | Electrolyzer $O_2$ gas |
| 530 | Heat from and/or to electrolyzer |
| 540 | $O_2$ gas for external applications |
| 550 | Makeup water supply for electrolysis |
| 600 | Power Conditioner |
| 610 | Discharged electrical power |
| 620 | Power supply to equipment |
| 700 | Syngas Cleaner |
| 710 | Cleaned syngas for synthesis |
| 720 | Biochar and tar |
| 730 | Cleaned syngas for storage |
| 800 | Hydrocarbon Synthesizer |
| 810 | Synthetic hydrocarbons |
| 820 | Heat from or for hydrocarbon synthesis |
| 830 | Recycle mass |
| 840 | Combustible mass to genset |
| 900 | Genset |
| 910 | Electrical Power from genset |
| 920 | Mass and heat products of genset |

The Biomass Preparer 100 can prepare the particle size, density, and/or dryness of biomass feed 010 for storage prior to thermal decomposition. In certain embodiments, the biomass can be prepared and stored for approximately 8 hours or more before thermal decomposition. The biomass particle size can have at least one average dimension between approximately 1 and approximately 10 centimeter in length, a bulk density of approximately 0.2 to approximately 0.9 kilogram/liter, and/or a dryness of 0 to approximately 30 weight percent. Large-particle biomass can be chipped, shredded, ground, and/or otherwise reduced to meet the size requirements. Small-particle and/or low-density biomass can be densified and/or compacted into particles with equipment and/or methods that include, but are not limited to cubing, briquetting, and/or pelletizing to meet the size and/or density requirements for thermal decomposition. Heat 450 from the Biomass Thermal Decomposer 300, Hydrocarbon Synthesizer 800, Electrolyzer 500, and/or other sources can be used to dry and/or preheat the biomass. Gases that have oxygen gas ($O_2$) and/or carbon dioxide gas ($CO_2$) in concentrations greater than approximately 20 volume percent can be applied to displace the air's $N_2$ from within and/or around the biomass so that the nitrogen gas ($N_2$) content of the syngas 710 produced by thermal decomposition of biomass is less than approximately 30 volume percent. In certain embodiments, combustion of recycle mass 460 originating from the Hydrocarbon Synthesizer 800 with air and/or $O_2$ gas 470 concentrated to greater than approximately 90 volume percent can be applied to the prepared biomass 110 to preheat the biomass to temperatures greater than approximately 100 degrees Celsius. In certain embodiments, the recycle mass 830 and/or combustible mass 840 can be combusted with a Genset 900 to also produce electrical power in addition to preparing the biomass.

Renewable energy 020 can be supplied to the Renewable Power Generator 200 to produce approximately 0.1 to approximately 20 megawatts of electrical power. The electrical power can be generated via photovoltaic, solar thermal, hydrokinetic, geothermal, biological, nuclear, and/or other renewable electrical power and/or low-carbon electrical power generation located onsite and/or offsite. The Renewable Power Generator 200 can be co-located to deliver direct current (DC) and/or alternating current (AC) electrical power to the Electrolyzer 500, Power Conditioner 600, and/or other systems.

The Biomass Thermal Decomposer 300 can convert the prepared biomass 110 to a synthesis gas (syngas) that is predominantly composed of hydrogen ($H_2$), carbon monoxide (CO), carbon dioxide ($CO_2$) methane ($CH_4$), and/or nitrogen ($N_2$) gases. Prepared biomass 110 can be thermally decomposed by Biomass Thermal Decomposer 300 at temperatures of approximately 300 to approximately 1,200 degrees Celsius through gasification, pyrolysis, hydrolysis, liquefaction, oxidation, reduction, cracking, and/or other thermochemical processes. The thermally decomposed biomass 310 can comprise syngas and/or other products of thermal decomposition, e.g., liquids, such as tars, and/or solids, such as biochar and/or ash. In certain embodiments, via over approximately 60 weight percent of the prepared biomass 110 can be converted to syngas 710 using temperatures that can reach over 750 degrees Celsius. Purified $O_2$ 420, air 040, and/or some combination thereof can be used to support autothermal gasification in Biomass Thermal Decomposer 300. In certain embodiments where synthetic natural gas is the primary product of the hydrocarbon synthesis performed by Hydrocarbon Synthesizer 800, the gasifying agents can be composed of $O_2$ gas from 520, $CO_2$ gas from 310 and/or 830, steam ($H_2O$) from 830, and/or $H_2$ gas from 510 and/or 830, which can be controlled to produce a syngas 710 with less than approximately 5 volume percent $N_2$ and more than approximately 2 volume percent $CH_4$. In certain exemplary embodiments where liquifiable hydrocarbons are the primary product of the hydrocarbon synthesis performed by Hydrocarbon Synthesizer 800, the gasifying agent composition can produce a syngas 710 with a $N_2$ concentration of less than approximately 30 volume percent and $CH_4$ concentration of less than approximately 10 volume percent. In certain exemplary embodiments, recycle mass 430 from Hydrocarbon Synthesizer 800 that is routed to Biomass Thermal Decomposer 300 can include unreacted CO, unreacted $CO_2$, unreacted $H_2$, unreacted $CH_4$, fuel gas products of Fischer-Tropsch synthesis, oxygenated hydrocarbons with solubilities greater than approximately 1 weight percent in water, and/or other syngas components and/or synthesized hydrocarbons that are not monetized and/or otherwise used by the embodiment. In certain exemplary embodiments, biogas, natural gas, renewable natural gas, and/or another source of carbon can be input to Biomass Thermal Decomposer 300 in addition to or instead of biomass 110. Certain exemplary embodiments can operate Biomass Thermal Decomposer 300 at approximately steady-state input flow rates near its peak thermal decomposition input flow rates such that its annual average capacity (e.g., annual average input flow rate) is within approximately 70 to approximately 100 percent of its peak capacity (e.g., nameplate biomass input flow rate). Certain exemplary embodiments can operate Biomass Thermal Decomposer 300 at input flow rates that vary in response to the temporal variation in the availability of renewable energy and/or biomass 010 such that annual average capacity (e.g., average annual input flow rate) of Biomass Thermal Decomposer 300 is within approximately 20 to approximately 70 percent of its peak capacity (e.g., nameplate biomass input flow rate). Heat produced by the biomass thermal decomposition process and/or Biomass Thermal Decomposer 300 can be used for preheating the syngas 710 for hydrocarbon synthesizer 800, drying and/or preheating the biomass 110, and/or supplying thermal energy to Electrolyzer 500 that can operate at temperatures above approximately 200 degrees Celsius in certain embodiments.

Mass & Heat Integrator 400 can enable relatively small scales of hydrocarbon synthesis from biomass 010 (e.g., less than approximately 20,000 tonnes of biomass 010 consumed per year and/or less than approximately 10,000 tonnes of synthesized hydrocarbons 810 produced per year), which can allow system 1000 to respond and/or adapt to operational factors with greater speed, efficiency, and/or flexibility. Biomass Preparer 100, Renewable Power Generator 200, Biomass Thermal Decomposer 300, Electrolyzer 500, Power Conditioner 600, Syngas Cleaner 700, and/or Hydrocarbon Synthesizer 800 can operate independently and/or codependently in response to prepared biomass 110 production, renewable electrical power supply, weather, market factors, policy factors, maintenance, operator control, etc.

Mass & Heat Integrator 400 can provide the control, storage, and/or transfer of gases, liquids, solids, and/or heat between the subsystems and/or processes of system 1000. Mass & Heat Integrator 400 can store enough electrolyzer $H_2$ gas 510 to operate Hydrocarbon Synthesizer 800 at approximately 60 to approximately 100 percent peak capacity rate (e.g., hydrocarbon synthesizer nameplate hydrocarbon output flow rate) for up to 100 hours in certain embodiments. Mass & Heat Integrator 400 can store enough electrolyzer $O_2$ gas 520 to operate Biomass Thermal Decomposer 300 at approximately 60 to approximately 100 percent peak capacity rate (e.g., biomass thermal decomposer nameplate biomass input flow rate) for up to 100 hours in certain embodiments. In certain embodiments, the electrical power supply of the utility grid can be peak shaved by storing electrolyzer $H_2$ gas 510 and electrolyzer $O_2$ gas 520 during times of low cost and/or surplus electrical power available from external sources 030. Mass & Heat Integrator can store enough cleaned syngas 730 to operate Hydrocarbon Synthesizer 800 at approximately 60 to approximately 100 percent peak capacity rate (e.g., nameplate hydrocarbon output flow rate) for up to approximately 100 hours in certain embodiments. Mass & Heat Integrator 400 can store enough $H_2O$ produced through fuel synthesis 830 to operate the Electrolyzer 500 at approximately 60 to approximately 100 percent peak capacity rate (e.g., nameplate electrical power consumption rate) or higher for up to approximately 100 hours in certain embodiments. In certain embodiments, Mass & Heat Integrator 400 can store at least approximately 20 weight percent of the $H_2$, CO, $CO_2$, and/or hydrocarbons 830 that would exit Hydrocarbon Synthesizer 800 during 1 hour at its peak hydrocarbon synthesis rate (e.g., nameplate hydrocarbon output flow rate) for recycling to Biomass Preparer 100, Biomass Thermal Decomposer 300, Hydrocarbon Synthesizer 800, and/or Genset 900.

In certain embodiments, Mass & Heat Integrator 400 can store enough thermal energy 320/820 produced by Biomass Thermal Decomposer 300 and/or Hydrocarbon Synthesizer 800 to operate Electrolyzer 500 at temperatures greater than approximately 200 degrees Celsius at its peak capacity (e.g., electrolyzer nameplate electrical power consumption rate) for over approximately 1 hour. The thermal energy can be stored and/or transported as heated water, propylene glycol, ethylene glycol, glycol-based fluid, oil, synthetic hydrocarbon-based and/or silicone-based fluid, molten salt, liquid metal, gas, and/or other heat transfer fluid in containers such as tanks, pressure vessels, and/or piping, etc., any of which containers can be sufficiently thermally insulated to substantially reduce heat and/or energy losses from the heat transfer fluid. Mass & Heat Integrator 400 can store enough $O_2$ gas 470 and/or recycle mass 460 to operate the Biomass Preparer 100 for at least approximately 0.5 hours at its peak preparation rates (e.g., nameplate biomass input flow rate) in certain embodiments. Mass & Heat Integrator 400 can include software, controllers/process control computers, user interfaces, storage containers, piping, pumps, mixers, automatic and/or manual valves, heat exchangers, pressure regulators, instrumentation, and/or other components and/or capabilities that support overall system integration, control, operation, performance, and/or management.

Electrolyzer 500 can convert electrical energy (e.g., 610) into chemical energy through the electrolysis of water to electrolyzer $H_2$ gas 510 and electrolyzer $O_2$ gas 520. Heat 530 can be produced by the operation of Electrolyzer 500 in certain exemplary embodiments that utilize proton exchange membrane (PEM) electrolyzers, alkaline electrolyzers, and/or other technology that electrolyzes water at temperatures below approximately 200 degrees Celsius. The heat produced by water electrolysis can be used to heat electrolyzer $O_2$ gas 520 and/or electrolyzer $H_2$ gas 510. Heat 530 alternatively can be consumed by electrolysis in certain embodiments that operate an Electrolyzer 500 that utilizes solid oxide electrolytic cells and/or other technology that electrolyzes water at temperatures above approximately 200 degrees Celsius. Assuming a higher heating value of approximately 16 megajoules per kilogram of prepared biomass 110 and approximately 142 megajoules per kilogram of electrolyzer $H_2$ gas 510, then electrolyzer $H_2$ gas 510 can be produced at annual average rates of approximately 0 to approximately 350 percent of the rate of biomass thermal decomposition of biomass 110 to syngas 310 in certain embodiments where gaseous synthetic hydrocarbons 810, such as methane, ethane, and/or alkenes are the primary products of Hydrocarbon Synthesizer 800. Electrolyzer $H_2$ gas 510 can be produced at annual average rates of approximately 0 to approximately 250 percent of the rate of biomass thermal decomposition of biomass 110 to syngas 310 in certain embodiments where liquifiable synthetic hydrocarbons are the primary products of Hydrocarbon Synthesizer 800. Electrolyzer $O_2$ gas 520 can be produced at rates of approximately 0.1 to approximately 0.8 tonne $O_2$ per 1 tonne of biomass 110 converted to syngas 310 in certain exemplary embodiments. Certain exemplary embodiments can operate Electrolyzer 500 near its peak electrolysis rate (e.g., electrolyzer nameplate electrical power consumption rate) such that annual average capacity (e.g., annual average electrolyzer electrical power consumption rate) is within approximately 70 to approximately 100 percent of its maximum annual capacity (e.g., electrolyzer maximum annual power consumption rate). Certain other embodiments can operate Electrolyzer 500 at rates that vary in response to the temporal variation in renewable energy 010 such that its annual average capacity (e.g., annual average electrolyzer electrical power consumption rate) is within approximately 20 to approximately 70 percent of its maximum annual capacity (e.g., maximum annual electrolyzer electrical power consumption rate). Electrolyzer $H_2$ gas 510 and electrolyzer $O_2$ gas 520 can be produced at pressures greater than approximately 4 bar in certain exemplary embodiments and greater than approximately 25 bar in certain other exemplary embodiments.

Power Conditioner 600 can enable a more steady supply of electrical power 610 to Electrolyzer 500 than unconditioned electrical power supplied directly from Renewable Power Generator 200. In certain exemplary embodiments, the electrical power requirements of system 1000 can be supplied by the source of renewable energy 020. Yet renewable energy 020 can have intermittent and/or variable character. For example, on a daily basis, a Renewable Power Generator 200 comprised of photovoltaic solar electrical power generation can produce up to approximately 7 hours of electrical power output near peak capacity near midday, have rapid decreases in electrical power output due to scattered cloud effects, and/or produce almost no electrical power for more than approximately 12 hours (e.g., overnight). In certain embodiments, Power Conditioner 600 can supply additional electrical power 030 from an external source, such as the utility grid, to stabilize the electrical power 610 supplied to Electrolyzer 500 if weather effects cause increases or decreases in electrical power supply rates that exceed the electrolyzer manufacturer's specified rates for changing electrolysis rates. In certain embodiments where the annual average Electrolyzer 500 capacity (e.g., annual average electrolyzer electrical power consumption rate) is approximately 20 to approximately 70 percent of its peak capacity (e.g., electrolyzer nameplate electrical power consumption rate), Power Conditioner 600 can store electrical power through batteries, capacitors, compressed air energy storage, and/or other electrical energy storage technologies to peak shave the renewable energy supply 020 over approximately 0 to approximately 6 hours. Peak shaving the renewable electrical power supply 210 to the Electrolyzer 500 can enable an approximate 0 to approximately 60 percent reduction in its capacity (e.g., electrolyzer nameplate electrical power consumption rate) by lowering the maximum supply of electrical power to Electrolyzer 500 and/or increasing the duration of electrolysis. In certain embodiments, Power Conditioner 600 can supply additional electrical power from the utility grid and/or other external power source 030 to the renewable electrical power 210 so that the annual average Electrolyzer 500 capacity (e.g., average annual electrolyzer electrical power consumption rate) is approximately 70 to approximately 100 percent of its maximum annual capacity (e.g., electrolyzer nameplate electrical power consumption rate). In certain embodiments, both peak shaving with electrical power storage and additional electrical power supply from external sources can be used to increase annual average electrolysis rates. In certain exemplary embodiments, all of the electrical power provided to system 1000 can be supplied by the external electrical power source 030. In certain exemplary embodiments, Power Conditioner 600 can peak shave the utility grid by storing low-cost and/or surplus electricity 030 from external electrical power source. Power Conditioner 600 can include rectifiers, inverters, capacitors, inductors, transformers, and/or other equipment for controlling current, voltage, phase, and/or conversions between the AC and/or DC electrical power properties required for the various equipment, modules, machines, processes, systems, and/or other aspects of system 1000. In certain exemplary embodiments, Power Conditioner 600 can include electrical power storage to ensure safe and/or efficient operation of system 1000 and/or any of its components, subsystems, and/or processes in the event that the supply of external electrical power 030 fails to meet corresponding operational requirements.

Syngas Cleaner 700 can remove biomass thermal decomposition byproducts 320 that can decrease the performance of converting syngas 710 to synthetic hydrocarbons 810. Biomass thermal decomposition byproducts 720 that can be removed by Syngas Cleaner 700 can include biochar, ash, and/or other solids, tar and/or other liquids, nitrogenous compounds, sulfur compounds, separable minerals, materials that can poison the hydrocarbon synthesis catalysts, and/or materials that can otherwise adversely affect the hydrocarbon synthesis process. Syngas 310 can be cleaned for hydrocarbon synthesis through condensation, precipitation, filtration, absorption, adsorption, membranes, and/or other separation technologies. A biomass thermal decomposition byproduct 720 can be used as a soil amendment, fertilizer, and/or other agricultural and/or industrial application.

Hydrocarbon Synthesizer 800 can produce synthetic hydrocarbons 810 from syngas 710. Electrolyzer $H_2$ gas 440 can be supplied directly and/or indirectly (e.g., via Mass and Heat Integrator 400) to Hydrocarbon Synthesizer 800 to increase yields of synthetic hydrocarbons 810 in an exemplary embodiment. The ratio of $H_2$ to CO provided to Hydrocarbon Synthesizer 800 can be changed through selective catalysis of the water gas shift and/or reverse water gas shift reaction to increase yields of synthetic hydrocarbons 810 in certain embodiments. Hydrocarbon Synthesizer 800 can selectively catalyze the synthesis of methane, methanol, Fischer-Tropsch syncrude, and/or other initial synthetic hydrocarbons 810. The initial synthetic hydrocarbons 810 can be sold and/or used as is, purified, separated, refined, and/or converted to other synthetic hydrocarbons 810. For example, in certain embodiments, methanol can be converted to dimethyl ether and/or gasoline. In certain embodiments, Fischer-Tropsch syncrude can be separated and/or refined to gases, liquified petroleum gases (LPG), gasoline, jet fuel, diesel, heating oil, lubricant oil, wax, and/or other synthetic hydrocarbons. Syncrude and/or syncrude fractions can be cracked, polymerized, oligomerized, and/or converted via other refining processes onsite and/or offsite to produce higher value synthetic hydrocarbons in certain embodiments. For example, non-diesel components can be converted to diesel, non-jet fuel components can be converted to jet fuel, non-gasoline components can be converted to gasoline, etc. In certain exemplary embodiments, synthetic hydrocarbons 810 can be blended, finished, and/or otherwise prepared for use and/or transportation. Recycle mass 830 and/or heat 820 produced by Hydrocarbon Synthesizer 800 can be recycled to other processes in system 1000 by transfer to Mass & Heat Integrator 400. Recycled mass 820 can include $H_2$, CO, $CO_2$, $H_2O$, and/or synthetic hydrocarbons in certain embodiments. Hydrocarbon Synthesizer 800 can supply combustible mass 840, such as fuel gases and/or liquids, to Genset 900 for production of electrical power 910 and/or heat 920. Since the $N_2$ and $CO_2$ are generally inert during the synthetic hydrocarbon synthesis processes, their individual and/or combined concentrations can be used to control the production of heat and therefore reaction temperatures during synthetic hydrocarbon synthesis. System 1000 can be designed and used to keep the $N_2$ and/or $CO_2$ concentrations within the design and/or operational specifications of Hydrocarbon Synthesizer 800.

Genset 900 can generate electrical power 910 from recycle mass 830 and/or combustible mass 840 received from Hydrocarbon Synthesizer 800. Electricity 910 can be generated by an internal combustion engine-driven generator, turbine-driven generator, fuel cell, combined cycle generator, and/or other electrical power generation system. In certain exemplary embodiments, gaseous mass and/or heat 920 created via genset 920 can be recycled to Mass & Heat Integrator 400.

System 1000 can consume 0 to 20,000 tonnes of biomass 010 per year to synthesize 0 to 10,000 tonnes of synthetic hydrocarbons 810 per year. System 1000 can be scaled using one and/or more individual, modular, containerized, pallet-carried, and/or skid-mounted sub-systems. Each of the sub-systems can include balance of plant capabilities, be constructed off-site, be transported to the site in standardized shipping containers, and/or integrated with standardized, turn-key, installation methods. In certain exemplary embodiments, the value of the capital equipment manufactured off-site can be greater than approximately 60 percent of the total overall manufacturing fixed-capital investment in certain exemplary embodiments and greater than approximately 70 percent. In certain exemplary embodiments, Power Conditioner 600 can include approximately 0 to approximately 20 standard, premanufactured, battery modules that each: can be rated to produce approximately 0 to approximately 2 megawatts of electrical power; and/or can include balance of plant capabilities than can include electrical power converters, temperature regulation, and/or electronic control, etc. In certain exemplary embodiments, Electrolyzer 500 can comprise approximately 1 to approximately 20 standard, premanufactured, electrolysis modules that each: can be rated to consume approximately 0 to approximately 5 megawatts of electrical power; can be rated to produce approximately 0 to approximately 1,000 normal meters cubed of $H_2$ gas per hour; and/or can include balance of plant capabilities that can include electrical power rectifiers, water purification systems, gas purification systems, temperature control systems, and/or electronic process control systems. In certain exemplary embodiments, Biomass Thermal Decomposer 300 can comprise approximately 1 to approximately 20 standard, premanufactured, biomass thermal decomposition modules that each: can process approximately 0 to approximately 10 tonnes of input biomass 010 per day, can process approximately 0 to approximately 3 megawatts of biomass energy, and/or can be electronically controlled. In certain exemplary embodiments, Syngas Cleaner 700 can comprise approximately 1 to approximately 20 standard, premanufactured, syngas cleaning modules that each can be rated to produce approximately 0 to approximately 10 tonnes of cleaned syngas 720 per day. Hydrocarbon Synthesizer 800 can comprise approximately 1 to approximately 20 standard, premanufactured, hydrocarbon synthesizer modules that each: can be rated to produce approximately 0 to approximately 5 tonnes per day of diesel, gasoline, and/or other synthetic hydrocarbon products; can include hydrocarbon separation and/or refinement capabilities; and/or can be electronically controlled in certain embodiments. The number, types, and/or operational methods of modules can be changed over time to adapt to changes in biomass availability, resource availability, market factors, policy, and/or other factors that affect operation.

An exemplary embodiment composed of presently commercially available products can comprise a 1.8 megawatt generating photovoltaic array, a battery module rated for delivering 1 megawatt of electrical power over 4 hours (e.g., GE RSU-4000, Symtech Solar Megatron 1MW, EVESCO ES-10001000), a biomass densifier module capable of cubing 2 to 20 tonnes of biomass per hour (e.g., Warren&Baerg 200HD cuber), an automated biomass delivery module, a 1 megawatt-consuming PEM electrolyzer module (e.g., Siemens Silyzer 200, Cummins HyLYZER 200, H-TEC ME450, NEL MC250), a 0.6 megawatt-processing thermal biomass gasifier module (e.g., Proton Power ChyP, All Power Pallet, Syntech BioMax, Reset SyngaSmart, RE2 HKA 600), a 0.6 megawatt-processing thermal syngas cleaner module, 2 modules of a 0.3 tonnes of diesel production per day synthesizer (e.g., Ineratec Modular Chemical Plant, Compact GTL, OxEon Fischer Tropsch Reactor, T2C TriFTS), an air receiver tank with a 15,000 gallon water storage volume and 150 pounds per square inch pressure rating for $O_2$ gas storage, a module of 8 Type IV tanks each with a 7 meter cubed volume and rated for 275 bar of pressure for $H_2$ gas storage, and a 1,000 gallon water storage tank (e.g., Catec CT-0853, Hexagon TitanXL). Such an exemplary embodiment can be operated such that 1.8 megawatts of electrical power produced over 5 hours per day by the photovoltaic array can be peak shaved by the battery module to 1.0 megawatts of electrical power over 9 hours per day, the 1.0 megawatt PEM electrolyzer can be operated at 1.0 megawatts over 9 hours per day, the 9 hours of electrolysis can produce enough electrolyzer $H_2$ gas and electrolyzer $O_2$ gas to operate the gasifier, syngas cleaner, and diesel synthesizers near peak capacity over 24 hours per day, the $H_2$ gas and $O_2$ gas tanks can be used to peak shave the 9 hours per day of $H_2$ and $O_2$ gas production via electrolysis with another 15 hours of $H_2$ and $O_2$ gas storage for 24 hours of peak gasification and hydrocarbon synthesis rates, and the water tank can store enough water produced from 24 hours of fuel synthesis to supply 9 hours of water electrolysis. Such an exemplary embodiment can convert about 1,000 tonnes of biomass per year into approximately 100,000 gallons of diesel per year.

Figure 2:
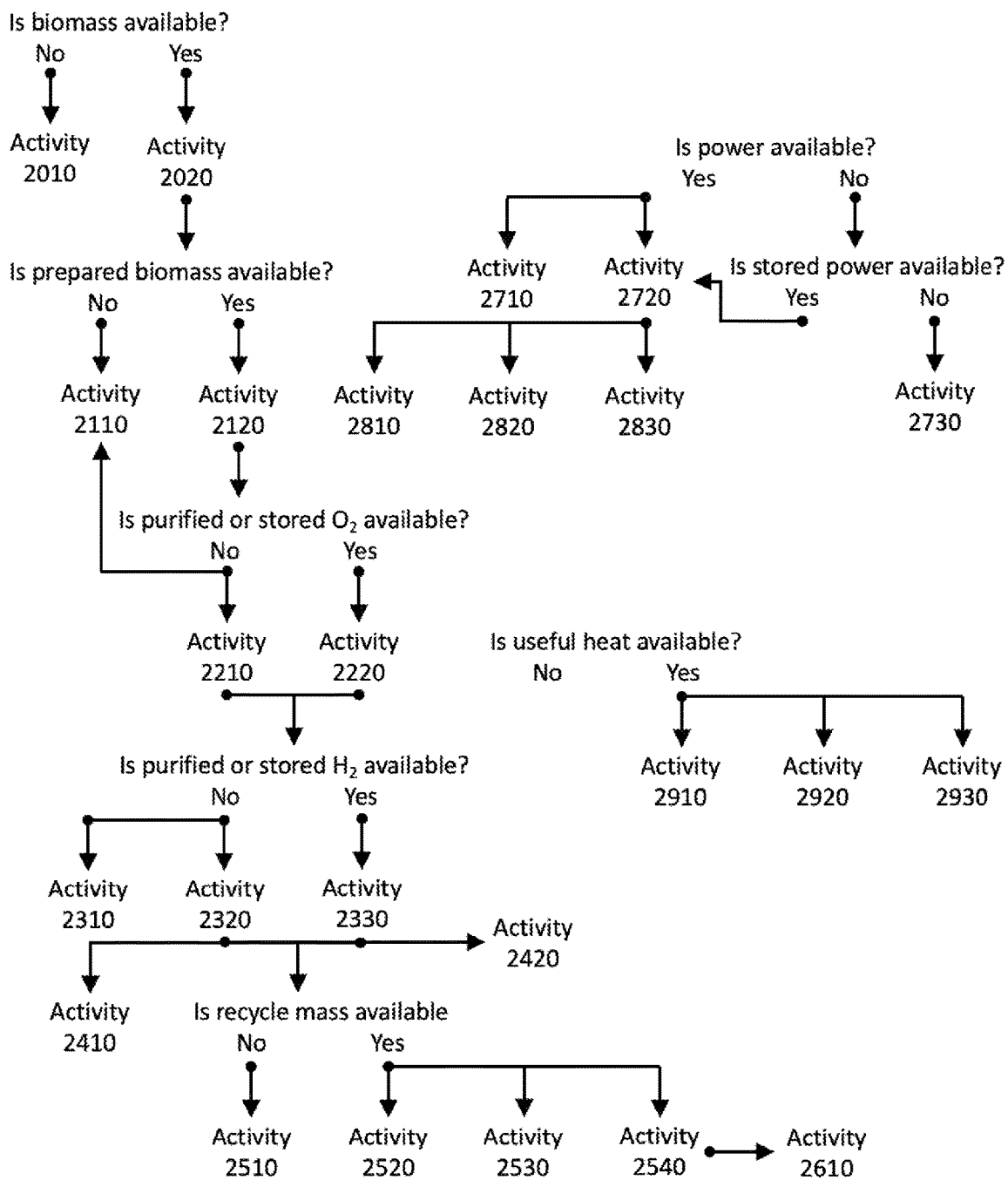
FIG. 2 is a flowchart of an exemplary embodiment of a method.

FIG. 2 is a flowchart of an exemplary embodiment of a method 2000. Referring to FIG. 2 and/or the below table of activities, at activity 2010, biomass feed can be provided. At activity 2020, provided biomass can be prepared and/or stored for thermal decomposition through densification, drying, etc. At activity 2110, the thermal decomposition process can be turned off because prepared biomass and/or purified $O_2$ are not available. At activity 2120, prepared biomass can be thermally decomposed. At activity 2210, the prepared biomass can be thermally decomposed with the addition of air to meet the oxygen demand because the supply of purified $O_2$ alone is insufficient. At activity 2220, the prepared biomass can be thermally decomposed with purified $O_2$. At activity 2310, the hydrocarbon synthesis process can be turned off because the supply of $H_2$ is insufficient. At activity 2320, synthetic hydrocarbons can be synthesized without the addition of $H_2$. At activity 2330, synthetic hydrocarbons can be synthesized with the addition of $H_2$. At activity 2410, synthesized hydrocarbons (e.g., fuel) can be stored onsite until distribution. At activity 2420, water coproduced by synthetic hydrocarbon synthesis can be sent directly to the electrolyzer and/or stored for water electrolysis. At activity 2510, the recycle process can be turned off because recycle mass is insufficiently available. At activity 2520, some or all of the recycle mass can be supplied to the thermal decomposition process. At activity 2530, some or all of the recycle mass can be stored. At activity 2550, some or all of the recycle mass can be supplied to the genset. At activity 2610, electrical power can be produced by the genset. At activity 2710, electricity from the onsite, renewable power supply and/or utility grid can be stored. At activity 2720, water electrolysis can be electrically powered by the available electricity and/or stored electrical power. At activity 2730, the water electrolysis process can be turned off. At activity 2810, useful heat can be stored for use at a later time. At activity 2810, the electrolyzer $H_2$ and/or electrolyzer $O_2$ can be stored for use at a later time. At activity 2820, electrolyzer $O_2$ can be sent to the thermal decomposer. At activity 2830, electrolyzer $H_2$ can be sent to the hydrocarbon synthesizer. At activity 2910, useful heat from any onsite source can be stored for use at a later time. At activity 2920, useful heat can be provided, such as via a heat exchanger, from any source (thermal decomposition, fuel synthesis, electrolysis, etc.) to any application (electrolysis, biomass, recycle mass, etc.). At activity 2930, useful heat can be discarded.

| | |
|---|---|
| 2010 | Procure biomass |
| 2020 | Prepare biomass for thermal decomposition |
| 2110 | Turn on thermal decomposition |
| 2120 | Thermally decompose biomass |
| 2210 | Thermally decompose biomass with air |
| 2220 | Thermally decompose biomass with purified $O_2$ |
| 2310 | Turn off hydrocarbon synthesis |
| 2320 | Synthesize hydrocarbons without $H_2$ |
| 2330 | Synthesize hydrocarbons with $H_2$ |
| 2410 | Store hydrocarbon products |
| 2420 | Recycle and/or store water for electrolysis |
| 2510 | Turn off mass recycle |
| 2520 | Recycle mass to thermal decomposition |
| 2530 | Store recycle mass |
| 2540 | Recycle mass to genset |
| 2610 | Generate electrical power |
| 2710 | Store electrical power |
| 2720 | Electrolyze water |
| 2810 | Store $H_2$ and/or $O_2$ gases |
| 2820 | Send $O_2$ to thermal decomposition |
| 2830 | Send $H_2$ to hydrocarbon synthesis |
| 2910 | Store heat |
| 2920 | Exchange heat |
| 2930 | Waste heat |

Figure 3:
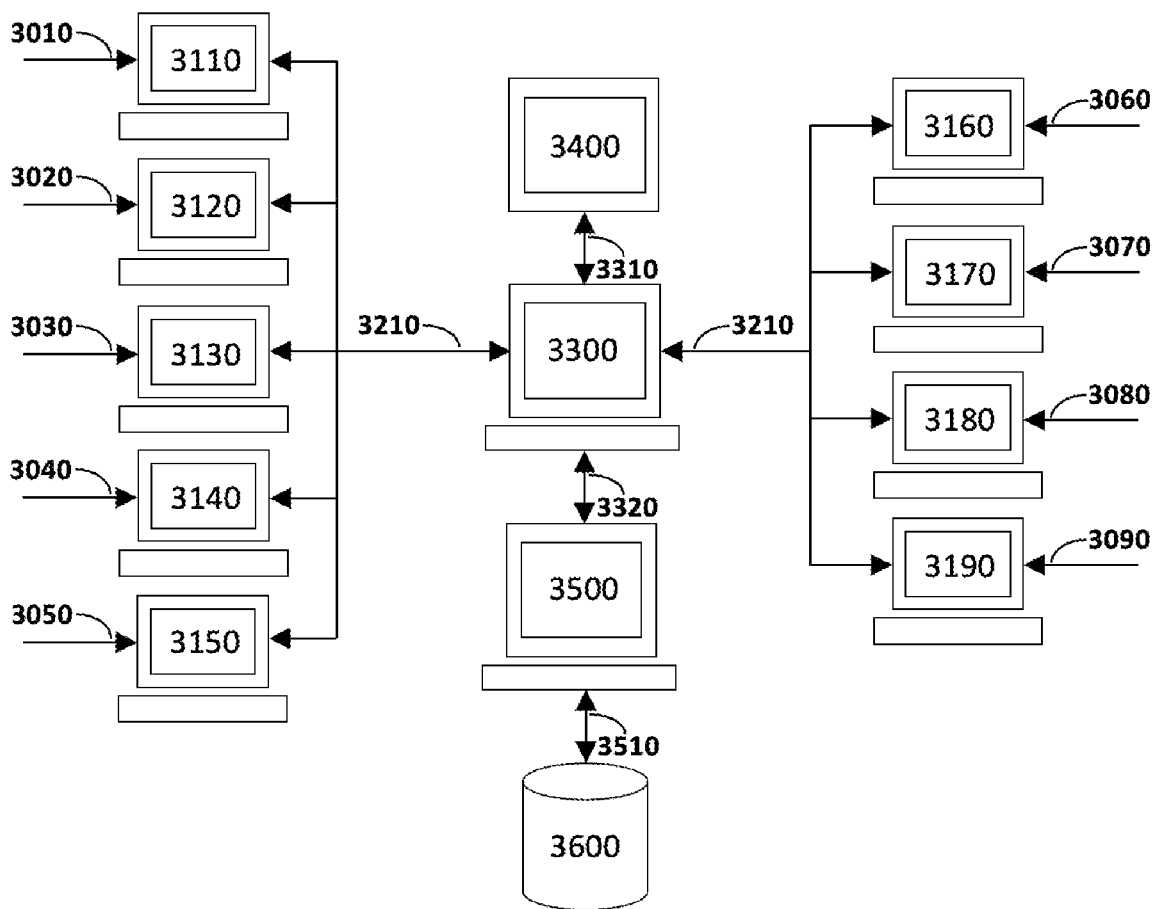
FIG. 3 is a block diagram of an exemplary embodiment of a process control system.

FIG. 3 is a block diagram of an exemplary embodiment of a system 3000, which can comprise a process control system. To describe certain exemplary embodiments of system 3000, in FIG. 3 (and the accompanying table below), a corresponding controller has been assigned for each of the nine blocks (which can comprise one or more devices, machines, apparatuses, subsystems, unit operations, and/or premanufactured modules) of system 1000 of FIG. 1. Some, most, and/or all of the FIG. 1 blocks can have its own controller as each of the blocks of FIG. 1 can be procured with its own control system. One controller can control more than one block in certain embodiments. For example, the Biomass Thermal Decomposer Controller 3130 can collectively control the Biomass Thermal Decomposer 300, Biomass Preparer 100, and the Syngas Cleaner 700 in certain embodiments. As another example, the Power Conditioner Controller 3160 can collectively control the Power Conditioner 600, Renewable Power Generator 200, and Genset 900 in certain embodiments. One or more of the controller blocks in FIG. 3 can encompass more than one controller in some embodiments. For example, system 1000 can include three Biomass Thermal Decomposer 300 modules and each module can include its own controller. The controllers 3110-3190 can perform actions based on the signals and/or inputs 3010-3090 received from and/or based on operator inputs, weight sensors, optical sensors, pressure sensors, temperature sensors, gas composition sensors, mass flow sensors, volumetric sensors, and/or inputs from the Onsite Controller 3300.

The Onsite Controller can communicate directly 3210 with one or more of block controllers 3110-3190. In certain embodiments, the Onsite Controller 3300 can communicate 3310 with one or more Mobile Controllers 3400 to enable mobile process monitoring and/or control by the operator. The Onsite Controller 3300 can communicate 3320 with an Offsite Controller 3500. The Offsite Controller 3500 can be located at a local and/or regional facility. The Offsite Controller 3500 can enable offsite operators to monitor and/or operate one or more system 1000s. The Offsite Controller 3500 can store 3510 information regarding the operation and/or performance of the System 1000 in an Offsite Database 3600. Advancements and/or optimizations with respect to operation and/or performance can be developed from the data compiled in the Offsite Database for distribution 3320 back to the Onsite Controller 3300 from the Offsite Controller 3500.

| | |
|---|---|
| 3010 | Inputs to Biomass Preparer controller |
| 3020 | Inputs to Renewable Power Generator controller |
| 3030 | Inputs to Biomass Thermal Decomposer controller |
| 3040 | Inputs to Mass & Heat Integrator controller |
| 3050 | Inputs to Electrolyzer controller |
| 3060 | Inputs to Power Conditioner controller |
| 3070 | Inputs to Syngas Cleaner controller |
| 3080 | Inputs to Hydrocarbon Synthesizer controller |
| 3090 | Inputs to Genset controller |
| 3110 | Biomass Preparer controller |
| 3120 | Renewable Power Generator controller |
| 3130 | Biomass Thermal Decomposer controller |
| 3140 | Mass & Heat Integrator controller |
| 3150 | Electrolyzer controller |
| 3160 | Power Conditioner controller |
| 3170 | Syngas Cleaner controller |
| 3180 | Hydrocarbon Synthesizer controller |
| 3190 | Genset controller |
| 3210 | Communication with Onsite Controller |
| 3300 | Onsite Controller |
| 3310 | Communication with Mobile Controller |
| 3320 | Communication with Offsite Controller |
| 3400 | Mobile Controller |
| 3500 | Offsite Controller |
| 3510 | Communication with Offsite Database |
| 3600 | Offsite Database |

Figure 4:
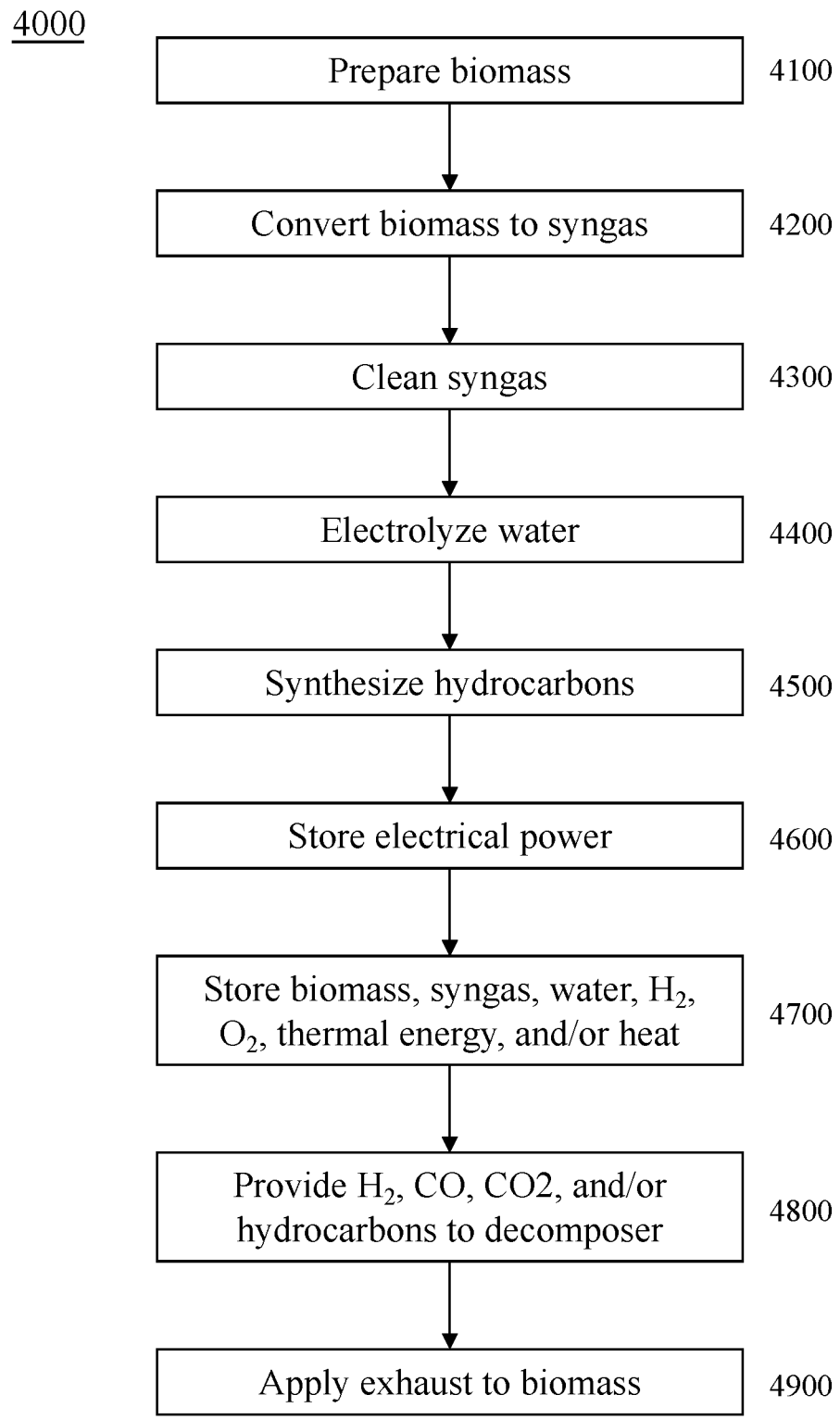
FIG. 4 is a flowchart of an exemplary embodiment of a method.

FIG. 4 is a flowchart of an exemplary embodiment of a method 4000. At activity 4100, a received biomass can be prepared (e.g., filtered, changed, and/or stored). At activity 4200, the prepared biomass can be converted to synthesis gas ("syngas"). At activity 4300, the syngas can be cleaned. At activity 4400, water can be electrolyzed into hydrogen gas and oxygen gas. At activity 4500, synthetic hydrocarbons can be synthesized from the (potentially cleaned) syngas and/or hydrogen gas. At activity 4600, electrical power can be stored. At activity 4700, received biomass, prepared biomass, syngas, cleaned syngas, water, hydrogen gas, oxygen gas, thermal energy, and/or heat can be stored. At activity 4800, hydrogen gas, carbon dioxide gas, carbon monoxide, hydrocarbons, and/or oxygenated hydrocarbons received from the hydrocarbon synthesizer can be provided to the biomass thermal decomposer. At activity 4900, exhaust heat and/or exhaust gas from the electrical power generator can be provided and/or applied to the prepared biomass.

Figure 5:
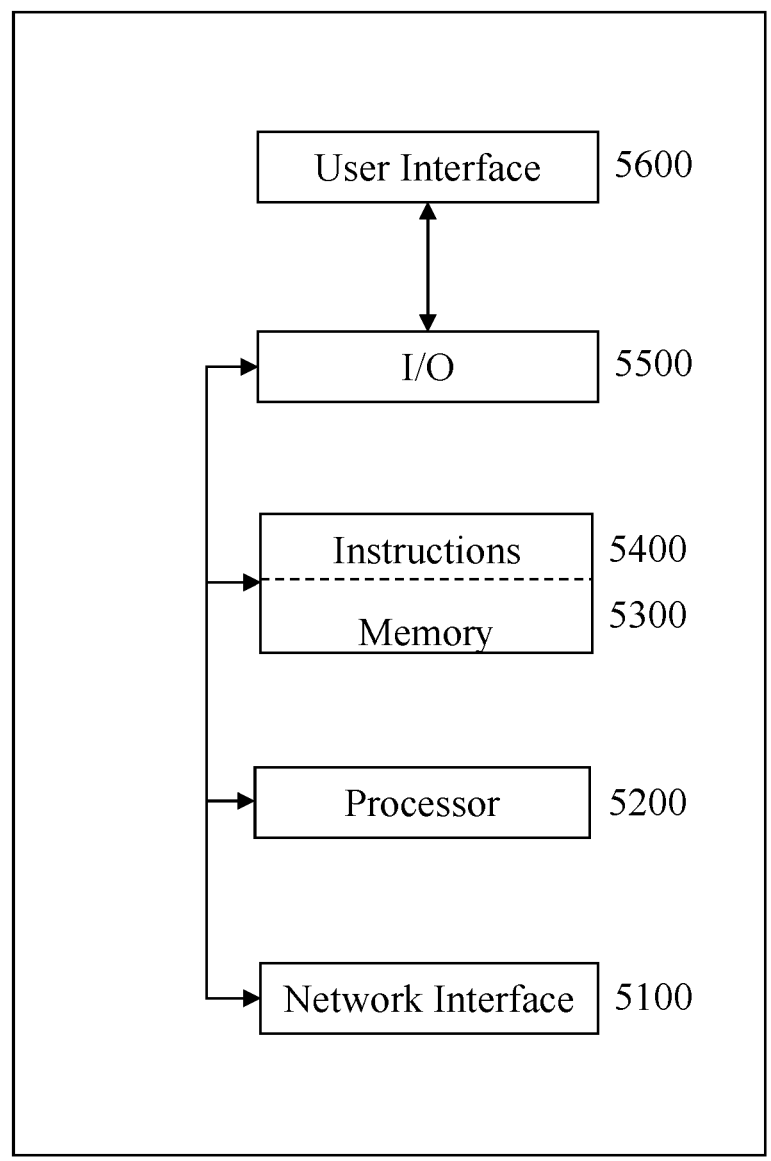
FIG. 5 is a block diagram of an exemplary embodiment of an information device.

FIG. 5 is a block diagram of an exemplary embodiment of an information device 5000, which in certain operative embodiments can comprise, for example, a server, user information device, controller, etc. Information device 5000 can comprise any of numerous transform circuits, which can be formed via any of numerous communicatively-, electrically-, magnetically-, optically-, fluidically-, and/or mechanically-coupled physical components, such as for example, one or more network interfaces 5100, one or more processors 5200, one or more memories 5300 containing instructions 5400, one or more input/output (I/O) devices 5500, and/or one or more user interfaces 5600 coupled to I/O device 5500, etc.

In certain exemplary embodiments, via one or more user interfaces 5600, such as a graphical user interface, a user can view a rendering of information related to researching, designing, modeling, creating, developing, making, building, manufacturing, assembling, operating, performing, using, modifying, maintaining, repairing, storing, marketing, offering for sale, selling, importing, exporting, distributing, delivering, selecting, specifying, requesting, ordering, buying, receiving, returning, rating, and/or recommending any of the blocks, systems, assemblies, components, devices, services, methods, user interfaces, and/or information described herein.

Certain exemplary embodiments can comprise a system configured for converting biomass to synthetic hydrocarbons, the system comprising:
  a biomass preparer configured to:
    filter and/or change a particle size, density, and/or dryness of a received biomass provided to the biomass preparer sufficiently for a resulting prepared biomass to have, on average, a maximum dimension between approximately 1 and approximately 10 centimeter, a bulk density between approximately 0.2 and approximately 0.9 kilogram/liter, and/or a dryness between 0 and approximately 30 weight percent; and/or
    store a volume of prepared biomass sufficient to operate the biomass thermal decomposer for at least 4 hours at approximately a biomass thermal decomposer nameplate biomass input flow rate;
  a biomass thermal decomposer configured to convert the prepared biomass to a synthesis gas;
  a synthesis gas cleaner configured to produce cleaned synthesis gas by removing biomass thermal decomposition byproducts from the synthesis gas;
  an electrolyzer configured to electrolyze water into electrolyzer hydrogen gas ($H_2$) and electrolyzer oxygen gas ($O_2$);
  a hydrocarbon synthesizer configured to produce synthetic hydrocarbons from the cleaned synthesis gas and the electrolyzer hydrogen gas;
  an electrical power conditioner configured to store sufficient electrical power selectively received from an electrical power generator and/or an external electrical power source to electrically power:
    the electrolyzer at approximately 20 percent to approximately 100 percent of an electrolyzer nameplate electrical power consumption rate for at least 0.5 hours; and/or
    the system at approximately 20 percent to approximately 100 percent of a system nameplate synthetic hydrocarbon output flow rate for at least 0.5 hours;
  a mass and heat integrator configured to store sufficient electrolyzer hydrogen gas to operate the hydrocarbon synthesizer at approximately 20 percent to approximately 100 percent of a hydrocarbon synthesizer nameplate synthetic hydrocarbon output flow rate for at least 0.5 hours; and/or
  the electrical power generator;
  wherein:
    the electrical power generator is configured to supply sufficient exhaust heat to heat the prepared biomass to at least 45 degrees Celsius;

the electrical power generator is configured to supply sufficient exhaust gas to decrease a concentration of the nitrogen ($N_2$) in the prepared biomass to less than 75 volume percent;

the mass and heat integrator is configured to store sufficient electrolyzer oxygen gas for the biomass thermal decomposer to produce the synthetic gas with a nitrogen ($N_2$) concentration of less than 20 volume percent at the biomass thermal decomposer nameplate biomass input flow rate for at least 0.5 hours;

the mass and heat integrator is configured to selectively provide electrolyzer hydrogen gas, carbon dioxide, carbon monoxide, and/or synthetic hydrocarbons to the biomass thermal decomposer;

the mass and heat integrator is configured to preheat the electrolyzer oxygen gas to at least 45 degrees Celsius and supply preheated electrolyzer oxygen gas to the biomass thermal decomposer;

the mass and heat integrator is configured to preheat recycle biomass to at least 45 degrees Celsius and to supply the preheated recycle biomass to the biomass thermal decomposer;

the mass and heat integrator is configured to provide water received from the hydrocarbon synthesizer to the electrolyzer;

the mass and heat integrator is configured to store sufficient water to operate the electrolyzer at approximately 20 percent to approximately 100 percent of the electrolyzer nameplate electrical power consumption rate for at least 0.5 hours;

the mass and heat integrator is configured to store at least 10 kilowatt hours of hydrocarbon synthesis mass byproducts;

the system is configured to control a ratio of hydrogen ($H_2$) to carbon monoxide (CO) in the synthesis gas to within a range of approximately 1.3 to approximately 2.7;

the electrical power conditioner is configured to store sufficient electrical power to operate the electrolyzer at approximately 100 percent of the electrolyzer nameplate electrical power consumption rate for at least 1 hour;

the electrical power generator, wherein the system is configured to store sufficient prepared biomass, sufficient electrical power, and sufficient electrolyzer hydrogen gas to operate:
the biomass thermal decomposer at approximately 70 percent to approximately 100 percent of the biomass thermal decomposer nameplate biomass input flow rate over a 2 hour period using electrical power received from only the electrical power generator; and/or
the hydrocarbon synthesizer at approximately 70 percent to approximately 100 percent of the hydrocarbon synthesizer nameplate synthetic hydrocarbon output flow rate over a 2 hour period using electrical power received from only the electrical power generator;

the electrolyzer is a solid oxide electrolysis cell and the mass and heat integrator is configured to store sufficient thermal energy to operate the electrolyzer at approximately 20 percent to approximately 100 percent of the electrolyzer nameplate electrical power consumption rate for at least 0.5 hours; and/or the system is configured to be at least partially controlled via an offsite controller.

Certain exemplary embodiments can comprise a method for converting biomass to synthetic hydrocarbons, the method comprising:
via a biomass preparer:
filtering and/or changing a particle size, density, and/or dryness of a received biomass provided to the biomass preparer sufficiently for a resulting prepared biomass to have, on average, a maximum dimension between approximately 1 and approximately 10 centimeter, a bulk density between approximately 0.2 and approximately 0.9 kilogram/liter, and/or a dryness between 0 and approximately 30 weight percent; and/or
storing a volume of prepared biomass sufficient to operate the biomass thermal decomposer for at least 4 hours at approximately a biomass thermal decomposer nameplate biomass input flow rate;
via a biomass thermal decomposer, converting the prepared biomass to a synthesis gas;
via a synthesis gas cleaner, producing cleaned synthesis gas by removing biomass thermal decomposition byproducts from the synthesis gas;
via an electrolyzer, electrolyzing water into electrolyzer hydrogen gas ($H_2$) and electrolyzer oxygen gas ($O_2$);
via a hydrocarbon synthesizer, producing synthetic hydrocarbons from the cleaned synthesis gas and the electrolyzer hydrogen gas;
via an electrical power conditioner, storing sufficient electrical power selectively received from an electrical power generator and/or an external electrical power source to electrically power:
the electrolyzer at approximately 20 percent to approximately 100 percent of an electrolyzer nameplate electrical power consumption rate for at least 0.5 hours; and/or
the system at approximately 20 percent to approximately 100 percent of a system nameplate hydrocarbon output flow rate for at least 0.5 hours;
via a mass and heat integrator, storing sufficient electrolyzer hydrogen gas provided by the electrolyzer to operate the hydrocarbon synthesizer at approximately 20 percent to approximately 100 percent of a hydrocarbon synthesizer nameplate synthetic hydrocarbon output flow rate for at least 0.5 hours;
via the mass and heat integrator, storing sufficient electrolyzer oxygen gas for the biomass thermal decomposer to produce the synthetic gas with a nitrogen ($N_2$) gas concentration of less than 20 volume percent at the biomass thermal decomposer nameplate biomass input flow rate for at least 0.5 hours;
via the mass and heat integrator, selectively providing hydrogen gas, carbon dioxide gas, carbon monoxide, and/or synthetic hydrocarbons to the biomass thermal decomposer;
supplying sufficient exhaust heat from the electrical power generator to heat the prepared biomass to at least 45 degrees Celsius;
supplying sufficient exhaust gas from the electrical power generator to decrease the concentration of nitrogen ($N_2$) in the prepared biomass to less than 75 volume percent;
preheating the electrolyzer oxygen to at least 45 degrees Celsius and supplying the preheated electrolyzer oxygen gas to the biomass thermal decomposer;
preheating recycle biomass to at least 45 degrees Celsius and supplying the preheated recycle biomass to the biomass thermal decomposer;

providing water received from the hydrocarbon synthesizer to the electrolyzer.

via the mass and heat integrator, storing sufficient water to operate the electrolyzer at approximately 20 percent to approximately 100 percent of the electrolyzer nameplate electrical power consumption rate for at least 0.5 hours;

via the mass and heat integrator, storing at least 10 kilowatt hours of hydrocarbon synthesis mass byproducts;

controlling a ratio of hydrogen ($H_2$) to carbon monoxide (CO) in the synthesis gas to within a range of approximately 1.3 to approximately 2.7;

via the electrical power conditioner, storing sufficient electrical power to operate the electrolyzer at approximately 100 percent of the electrolyzer nameplate electrical power consumption rate for at least 1 hour;

storing sufficient prepared biomass, sufficient electrical power, and sufficient electrolyzer hydrogen gas to operate:

the biomass thermal decomposer at approximately 70 percent to approximately 100 percent of the biomass thermal decomposer nameplate biomass input flow rate over a 2 hour period using electrical power received from only the electrical power generator; and/or the hydrocarbon synthesizer at approximately 70 percent to approximately 100 percent of the hydrocarbon synthesizer nameplate synthetic hydrocarbon output flow rate over a 2 hour period using electrical power from only the electrical power generator;

via the mass and heat integrator, storing sufficient thermal energy to operate the electrolyzer at approximately 20 percent to approximately 100 percent of the electrolyzer nameplate electrical power consumption rate for at least 0.5 hours, wherein the electrolyzer is a solid oxide electrolysis cell; and/or at least partially controlling operation of the system via an offsite controller.

Definitions

When the following phrases are used substantively herein, the accompanying definitions apply. These phrases and definitions are presented without prejudice, and, consistent with the application, the right to redefine these phrases via amendment during the prosecution of this application or any application claiming priority hereto is reserved.

For the purpose of interpreting a claim of any patent that claims priority hereto, each definition in that patent functions as a clear and unambiguous disavowal of the subject matter outside of that definition.

a—at least one.
about—around and/or approximately.
above—at a higher level.
acid—a compound capable of neutralizing alkalis and reddening blue litmus paper, containing hydrogen that can be replaced by a metal or an electropositive group to form a salt, or containing an atom that can accept a pair of electrons from a base. Acids are proton donors that yield hydronium ions in water solution, or electron-pair acceptors that combine with electron-pair donors or bases.
across—from one side to another.
activity—an action, act, step, and/or process or portion thereof.
adapt—to design, make, set up, arrange, shape, configure, and/or make suitable and/or fit for a specific purpose, function, use, and/or situation.
adapter—a device used to effect operative compatibility between different parts of one or more pieces of an apparatus or system.
after—following in time and/or subsequent to.
air—the earth's atmospheric gas.
along—through, on, beside, over, in line with, and/or parallel to the length and/or direction of; and/or from one end to the other of.
anaerobic—a condition where molecular oxygen is substantially absent.
and—in conjunction with.
and/or—either in conjunction with or in alternative to.
any—one, some, every, and/or all without specification.
apparatus—an appliance or device for a particular purpose.
approximately—about and/or nearly the same as.
around—about, surrounding, and/or on substantially all sides of; and/or approximately.
as long as—if and/or since.
as—built drawings—the revised sets of drawings marked-up by the manufacturer or contractor preparing a facility, piece of equipment, or project that report all changes made during the preparation process that describe deviation between the original design and what was actually built.
associate—to join, connect together, and/or relate.
at—in, on, and/or near.
at least—not less than, and possibly more than.
automatic—performed via an information device in a manner essentially independent of influence and/or control by a user. For example, an automatic light switch can turn on upon "seeing" a person in its "view", without the person manually operating the light switch.
average—a value obtained by dividing the sum of a set of quantities by the number of quantities in a set and/or an approximation of a statistical expected value.
axis—a straight line about which a body and/or geometric object rotates and/or can be conceived to rotate and/or a center line to which parts of a structure and/or body can be referred.
balance of plant—all the supporting components and auxiliary systems of a power plant and/or power module needed to deliver energy, other than the generating unit itself. These supporting components and/or auxiliary systems can include transformers, inverters, switching and control equipment, protection equipment, power conditioners, supporting structures etc., depending on the type of plant or module.
based on—indicating one or more factors that affect a determination, but not necessarily foreclosing additional factors that might affect that determination.
between—in a separating interval and/or intermediate to.
biomass—organic material that originates from one or more living organisms and has an average energy content of approximately 16 megajoules per ton of dry weight.
biomass preparer—a machine configured to filter, store, and/or change a particle size, density, and/or dryness of biomass.
Boolean logic—a complete system for logical operations.
bulk density—a property of a collection of particles, such as powders, granules, and other "divided" solids, defined as the mass of the collection divided by the total volume it occupies, where the total volume includes particle volume, inter-particle void volume, and internal pore volume.

by—via and/or with the use and/or help of.

byproduct—something produced in the making of something else.

capacity—the maximum rate of production and/or the ability to yield.

can—is capable of, in at least some embodiments.

cause—to bring about, provoke, precipitate, produce, elicit, be the reason for, result in, and/or effect.

cell—any device in which electrolysis occurs; a cell containing an electrolyte through which an externally generated electric current is passed by a system of electrodes in order to produce an electrochemical reaction.

centimeter—a metric unit of length equal to one hundredth of a meter.

change—(v.) to cause to be different; (n.) the act, process, and/or result of altering and/or modifying.

circuit—a physical system comprising, depending on context: an electrically conductive pathway; an information transmission mechanism; and/or a communications connection established via a switching device (such as a switch, relay, transistor, and/or logic gate, etc.) and/or established across two or more switching devices comprised by a network and between corresponding end systems connected to, but not comprised by the network.

clean—to rid of or reduce dirt, rubbish, and/or impurities.

composition of matter—a combination, reaction product, compound, mixture, formulation, material, and/or composite formed by a human and/or automation from two or more substances and/or elements.

compound—a pure, macroscopically homogeneous substance consisting of atoms or ions of two or more different elements in definite proportions that cannot be separated by physical methods. A compound usually has properties unlike those of its constituent elements.

comprising—including but not limited to.

conceive—to imagine, conceptualize, form, and/or develop in the mind.

concentration—a measure of how much of a given substance is mixed, dissolved, contained, and/or otherwise present in and/or with another substance, and/or a measure of the amount of dissolved substance contained per unit of volume and/or the amount of a specified substance in a unit amount of another substance, both measures defining a structure of a composition that comprises both substances.

condition—(n.) a mode, state of being, situation, and/or circumstance; (v.) to cause to be in a particular mode, state, situation, and/or circumstance.

configure—to design, arrange, set up, shape, and/or make suitable and/or fit for a specific purpose, function, use, and/or situation.

configured to—designed, arranged, set up, shaped, and/or made suitable and/or fit for a specific purpose, function, use, and/or situation, and/or having a structure that, during operation, will perform the indicated activity(ies). To the extent relevant to the current application, the use of "configured to" is expressly not intended to invoke 35 U.S.C. § 112 (f) for that structure.

connect—to join or fasten together.

consumption—usage.

containing—including but not limited to.

control—(n) a mechanical or electronic device used to operate a machine within predetermined limits; (v) to exercise authoritative and/or dominating influence over, cause to act in a predetermined manner, direct, adjust to a requirement, and/or regulate.

conversion—the process of and/or result of converting.

convert—to transform, adapt, and/or change, such as from a first form to a second form.

corresponding—related, associated, accompanying, similar in purpose and/or position, conforming in every respect, and/or equivalent and/or agreeing in amount, quantity, magnitude, quality, and/or degree.

coupleable—capable of being joined, connected, and/or linked together.

coupling—linking in some fashion.

create—to bring into being.

cycle—a set of predetermined activities.

data—distinct pieces of information, usually formatted in a special or predetermined way and/or organized to express concepts, and/or represented in a form suitable for processing by an information device.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

decrease—to be smaller in magnitude.

define—to establish the meaning, relationship, outline, form, and/or structure of; and/or to precisely and/or distinctly describe and/or specify.

degrees Celsius—a unit of temperature. The Celsius temperature scale defines the freezing point of water is 0 degrees, and the boiling point is 100 degrees at standard atmospheric pressure.

density—a measure of a physical quantity of something per unit measure, especially per unit length, area, or volume; the mass per unit volume of a substance under specified conditions of pressure and temperature; a measure of the compactness of a substance, expressed as its mass per unit volume.

derive—to receive, obtain, and/or produce from a source and/or origin.

determine—to find out, obtain, calculate, decide, deduce, ascertain, and/or come to a decision, typically by investigation, reasoning, and/or calculation.

device—a machine, manufacture, and/or collection thereof.

digital—non-analog and/or discrete.

dimension—an extension in a given direction and/or a measurement in length, width, or thickness.

dryness—the condition of not containing liquid water.

each—every one of a group considered individually.

effective—sufficient to bring about, provoke, elicit, and/or cause.

electrical—relating to producing, distributing, and/or operating by electricity.

electrolysis—a process that is characterized by conduction of an electric current between two or more electrodes through an electrolyte and resulting in a chemical change (e.g., oxidation, reduction, etc.) (other than that brought about by the mere heating effect of the electric current) at one or more of the electrodes (e.g., electrolytic coating or etching, etc.) or at another location in contact with the electrolyte as a direct result of the electric current passing therethrough (e.g., electrolytic material treatment, etc.), such chemical change being the process objective and not merely as a means of conducting an electric current through the electrolyte.

electrolyze—to cause to decompose by electrolysis.

electrolyzer—an apparatus in which electrolysis is carried out, the apparatus comprising one or many electrolytic cells.

elemental—of, relating to, or denoting a chemical element.

embodiment—an implementation, manifestation, and/or concrete representation.

energy—usable power; a measurable physical quantity, with dimensions equivalent and/or convertible to mass times velocity squared, that is conserved for an isolated system.

entrain—to carry along in a current.

estimate—(n) a calculated value approximating an actual value; (v) to calculate and/or determine approximately and/or tentatively.

exemplary—serving as an example, instance, and/or illustration.

exhaust heat—heat generated during and/or from a chemical reaction external—exterior and/or relating to, existing on, and/or connected with the outside and/or or an outer part.

filter—(n) a device that removes something from whatever passes through it; (v) to remove something by passing through a filter; to remove, from a first substance, a second substance entrained, suspended, mixed, and/or present in the first substance, by passing the first substance through a filter, where the second substance differs from the first substance in composition and/or property.

first—a label for a referenced element in one or more patent claims, but that label does not necessarily imply any type of ordering to how that element (or any other elements of a similar type) is implemented in embodiments of the claimed subject matter.

flow—(n) a stream and/or current; (v) to move and/or run smoothly with unbroken continuity, as in the manner characteristic of a fluid.

flow rate—an amount of a composition provided to a particular place within a stated time period.

for—with a purpose of.

from—used to indicate a source, origin, and/or location thereof.

fuel—a substance that produces useful energy when it undergoes a chemical or nuclear reaction.

fuel gas—a combustible gaseous composition that releases heat upon oxidation, the composition comprising one or more of hydrogen, carbon monoxide, and methane.

further—in addition.

gas—a substance and/or collection of substances (e.g., molecules, atoms, ions, and/or electrons, etc.) in a gaseous state, that is, in a state of matter distinguished from the solid and liquid states by relatively low density and viscosity, relatively great expansion and contraction with changes in pressure and temperature, the ability to diffuse readily, and the spontaneous tendency to become distributed uniformly throughout any container.

generate—to create, produce, give rise to, and/or bring into existence.

given—identified, specified, selected, fixed, particular, and/or previously stated.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

have—to possess as a characteristic, quality, or function.

having—including but not limited to; possessing as a characteristic, quality, or function.

heat—(n.) energy associated with the motion of atoms and/or molecules and capable of being transmitted through solid media and fluid media by conduction, through fluid media by convection, and/or through fluid media and/or empty space by radiation; (v.) to transfer energy from one substance to another resulting in an increase in temperature of one substance.

human—machine interface-hardware and/or software adapted to render information to a user and/or receive information from the user; and/or a user interface.

hydrocarbon—an organic compound containing hydrogen and carbon.

hydrocarbon synthesizer-a device, machine, and/or system configured to produce synthetic hydrocarbons and/or oxygenated hydrocarbons from a synthesis gas.

hydrogen—an element defined by each atom comprising a single proton and a single electron.

including—including but not limited to.

information device—any device capable of processing data and/or information, such as any general purpose and/or special purpose computer, such as a personal computer, workstation, server, minicomputer, mainframe, supercomputer, network device, Internet appliance, computer terminal, laptop, tablet computer (such as an iPad-like device), wearable computer, Personal Digital Assistant (PDA), mobile terminal, Bluetooth device, communicator, "smart" phone (such as an iPhone-like device), messaging service (e.g., Blackberry) receiver, pager, facsimile, cellular telephone, traditional telephone, telephonic device, video or still camera, embedded controller, programmed microprocessor or microcontroller and/or peripheral integrated circuit elements, ASIC or other integrated circuit, hardware electronic logic circuit such as a discrete element circuit, and/or programmable logic device such as a PLD, PLA, FPGA, or PAL, or the like, etc. In general, any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc. In information device can be a component of and/or augment another device and/or system, such as an appliance, machine, tool, robot, vehicle, television, printer, "smart" utility meter, etc. (even though that device and/or system might not be illustrated or described), and/or, in some embodiments, can function in stand-alone mode.

initialize—to prepare something for use and/or some future event.

input—something entering a system, process, machine, and/or device.

input/output (I/O) device—any device adapted to provide input to, and/or receive output from, an information device. Examples can include an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, switch, relay, haptic device, vibrator, tactile simulator, and/or tactile pad, potentially including a port to which an I/O device can be attached or connected.

install—to connect or set in position and prepare for use.

instructions—directions, which can be implemented as hardware, firmware, and/or software, the directions adapted to perform a particular operation and/or function via creation and/or maintenance of a predetermined physical circuit.

into—to a condition, state, and/or form of; toward, in the direction of, and/or to the inside of.

ion—an electrically charged atom or group of atoms formed by the loss or gain of one or more electrons, as a cation (positive ion), which is created by electron loss and is attracted to the cathode in electrolysis, or as an anion (negative ion), which is created by an electron gain and is attracted to the anode. The valence of an ion is equal to the number of electrons lost or gained and is indicated by a plus sign for cations and a minus sign for anions, thus: Na+, Cl−, Ca++, S=.

is—to exist in actuality.

kilowatt—a unit of power equivalent to one thousand Watts.

less than—having a measurably smaller magnitude and/or degree as compared to something else.

link—a physical or logical communication channel, such as between one or more network nodes or between one or more transmitters and one or more receivers, that connects two or more communicating devices by means of wired, wireless, microwave, satellite, cellular, radio, spread spectrum, optical, and/or television signals.

logic gate—a physical device adapted to perform a logical operation on one or more logic inputs and to produce a single logic output, which is manifested physically. Because the output is also a logic-level value, an output of one logic gate can connect to the input of one or more other logic gates, and via such combinations, complex operations can be performed. The logic normally performed is Boolean logic and is most commonly found in digital circuits. The most common implementations of logic gates are based on electronics using resistors, transistors, and/or diodes, and such implementations often appear in large arrays in the form of integrated circuits (a.k.a., IC's, microcircuits, microchips, silicon chips, and/or chips). It is possible, however, to create logic gates that operate based on vacuum tubes, electromagnetics (e.g., relays), mechanics (e.g., gears), fluidics, optics, chemical reactions, and/or DNA, including on a molecular scale. Each electronically-implemented logic gate typically has two inputs and one output, each having a logic level or state typically physically represented by a voltage. At any given moment, every terminal is in one of the two binary logic states ("false" (a.k.a., "low" or "0") or "true" (a.k.a., "high" or "1"), represented by different voltage levels, yet the logic state of a terminal can, and generally does, change often, as the circuit processes data. Thus, each electronic logic gate typically requires power so that it can source and/or sink currents to achieve the correct output voltage. Typically, machine-implementable instructions are ultimately encoded into binary values of "0"'s and/or "1"s and, are typically written into and/or onto a memory device, such as a "register", which records the binary value as a change in a physical property of the memory device, such as a change in voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc. An exemplary register might store a value of "01101100", which encodes a total of 8 "bits" (one byte), where each value of either "0" or "1" is called a "bit" (and 8 bits are collectively called a "byte"). Note that because a binary bit can only have one of two different values (either "0" or "1"), any physical medium capable of switching between two saturated states can be used to represent a bit. Therefore, any physical system capable of representing binary bits is able to represent numerical quantities, and potentially can manipulate those numbers via particular encoded machine-implementable instructions. This is one of the basic concepts underlying digital computing. At the register and/or gate level, a computer does not treat these "0"s and "1"s as numbers per se, but typically as voltage levels (in the case of an electronically-implemented computer), for example, a high voltage of approximately +3 volts might represent a "1" or "logical true" and a low voltage of approximately 0 volts might represent a "0" or "logical false" (or vice versa, depending on how the circuitry is designed). These high and low voltages (or other physical properties, depending on the nature of the implementation) are typically fed into a series of logic gates, which in turn, through the correct logic design, produce the physical and logical results specified by the particular encoded machine-implementable instructions. For example, if the encoding request a calculation, the logic gates might add the first two bits of the encoding together, produce a result "1" ("0"+"1"="1"), and then write this result into another register for subsequent retrieval and reading. Or, if the encoding is a request for some kind of service, the logic gates might in turn access or write into some other registers which would in turn trigger other logic gates to initiate the requested service.

logical—a conceptual representation.

longitudinal—of and/or relating to a length; placed and/or running lengthwise.

longitudinal axis-a straight line defined parallel to an object's length and passing through a centroid of the object.

machine-implementable instructions—directions adapted to cause a machine, such as an information device, to perform one or more particular activities, operations, and/or functions via forming a particular physical circuit. The directions, which can sometimes form an entity called a "processor", "kernel", "operating system", "program", "application", "utility", "subroutine", "script", "macro", "file", "project", "module", "library", "class", and/or "object", etc., can be embodied and/or encoded as machine code, source code, object code, compiled code, assembled code, interpretable code, and/or executable code, etc., in hardware, firmware, and/or software.

machine-readable medium—a transitory and/or non-transitory physical and/or tangible structure via which a machine, such as an information device, computer, microprocessor, and/or controller, etc., can store or carry one or more machine-implementable instructions, data structures, data, and/or information and/or obtain one or more stored machine-implementable instructions, data structures, data, and/or information. Examples include a memory device, punch card, player-piano scroll, etc.

manmade—a tangible physical item that is synthetic and/or made by humans rather than occurring in nature.

mass—a property of matter equal to the measure of the amount of matter contained in or constituting a physical body that partly determines the body's resistance to changes in the speed or direction of its motion.

mass and heat integrator—one or more devices, machines, and/or systems configured to store mass and/or heat (themal energy).

mass byproduct—a byproduct that has mass (e.g., a byproduct other than heat, electricity, or other form of energy).

mass-to-mass ratio—the mass of a first substance expressed with respect to the mass of a second substance.

maximum—out of a sequence of data points, the data point having the largest magnitude as measured along the non-time axis; a measure of the magnitude of such a data point.

may—is allowed and/or permitted to, in at least some embodiments.

medium—any substance or material, such as one or more solids, liquids, vapors, fluids, water, and/or air, etc.

memory device—an apparatus capable of storing, sometimes permanently, machine-implementable instructions, data, and/or information, in analog and/or digital format. Examples include at least one non-volatile memory, volatile memory, register, relay, switch, Random Access Memory, RAM (e.g., SDRAM, DDR, RDRAM, and/or SRAM, etc.), Read Only Memory, Erasable Programmable Read-Only Memory (EPROM), Electrically Erasable Programmable Read-Only Memory (EEPROM), ROM, flash memory, magnetic media, hard disk, floppy disk, magnetic tape, optical media, optical disk, compact disk, CD, digital versatile disk, DVD, and/or raid array, etc. The memory device can be coupled to a processor and/or can store and provide instructions adapted to be executed by processor, such as according to an embodiment disclosed herein.

meter—a device adapted to detect and/or record a measured value.

method—one or more acts that are performed upon subject matter to be transformed to a different state or thing and/or are tied to a particular apparatus, said one or more acts not a fundamental principal and not preempting all uses of a fundamental principal.

milligram—One one-thousandth of a gram.

mix—to combine and/or blend into one mass, stream, and/or mixture.

molecule—the smallest particle of a substance that retains the chemical and physical properties of the substance and is composed of two or more atoms; and/or a group of like or different atoms held together by chemical forces.

nameplate—an as-designed, as-built, or as-installed full-load property of a facility, piece of equipment, subsystem, block, module, and/or process unit at approximately steady state conditions. Also known as a rated capacity, nominal capacity, design capacity, installed capacity, or maximum property, that property sometimes referred to as a "capacity", and depending on context, the property itself being, e.g., a throughput, flow rate, power input, or power output, etc.

network—a communicatively coupled plurality of nodes, communication devices, and/or information devices. Via a network, such nodes and/or devices can be linked, such as via various wireline and/or wireless media, such as cables, telephone lines, power lines, optical fibers, radio waves, and/or light beams, etc., to share resources (such as printers and/or memory devices), exchange files, and/or allow electronic communications therebetween. A network can be and/or can utilize any of a wide variety of sub-networks and/or protocols, such as a circuit switched, public-switched, packet switched, connection-less, wireless, virtual, radio, data, telephone, twisted pair, POTS, non-POTS, DSL, cellular, telecommunications, video distribution, cable, radio, terrestrial, microwave, broadcast, satellite, broadband, corporate, global, national, regional, wide area, backbone, packet-switched TCP/IP, IEEE 802.03, Ethernet, Fast Ethernet, Token Ring, local area, wide area, IP, public Internet, intranet, private, ATM, Ultra Wide Band (UWB), Wi-Fi, BlueTooth, Airport, IEEE 802.11, IEEE 802.11a, IEEE 802.11b, IEEE 802.11g, X-10, electrical power, 3G, 4G, multi-domain, and/or multi-zone sub-network and/or protocol, one or more Internet service providers, one or more network interfaces, and/or one or more information devices, such as a switch, router, and/or gateway not directly connected to a local area network, etc., and/or any equivalents thereof.

network interface—any physical and/or logical device, system, and/or process capable of coupling an information device to a network. Exemplary network interfaces comprise a telephone, cellular phone, cellular modem, telephone data modem, fax modem, wireless transceiver, communications port, ethernet card, cable modem, digital subscriber line interface, bridge, hub, router, or other similar device, software to manage such a device, and/or software to provide a function of such a device.

no—an absence of and/or lacking any.

non-destructively—to perform substantially without damaging.

one—being and/or amounting to a single unit, individual, and/or entire thing, item, and/or object.

only—substantially without anything further.

operable—practicable and/or fit, ready, and/or configured to be put into its intended use and/or service.

operate—to perform a function and/or to work.

operative—when in operation for its intended use and/or service.

or—a conjunction used to indicate alternatives, typically appearing only before the last item in a group of alternative items.

organic—a compound containing carbon, which is further characterized by the presence in the molecule of two carbon atoms bonded together; or one atom of carbon bonded to at least one atom of hydrogen or halogen; or one atom of carbon bonded to at least one atom of nitrogen by a single or double bond.

other—a different and/or distinct entity and/or not the same as already mentioned and/or implied.

output—(n) something produced and/or generated; and/or the energy, power, work, signal, and/or information produced by a system; something produced in a given time period; (v) to provide, produce, manufacture, and/or generate.

outside—beyond a range, boundary, and/or limit; and/or not within.

over—with reference to, during, and/or throughout.

oxide—any compound of oxygen with another element.

oxygenated—chemical compounds contain oxygen as a part of their chemical structure.

packet—a generic term for a bundle of data organized in a specific way for transmission, such as within and/or across a network, such as a digital packet-switching network, and comprising the data to be transmitted and certain control information, such as a destination address.

parallel—of, relating to, and/or designating lines, curves, planes, and/or surfaces everywhere equidistant.

particle—a small piece or part. A particle can be and/or be comprised by a powder, bead, crumb, crystal, dust, grain, grit, meal, pounce, pulverulence, and/or seed, etc.

per—for each and/or by means of.

percent—one part in one hundred.

perceptible—capable of being perceived by the human senses.

period—a time interval.

perpendicular—intersecting at or forming substantially right angles.

pH—a measure representing the base 10 logarithm of the reciprocal of hydrogen ion concentration in gram atoms per liter, used to express the acidity or alkalinity of a solution on a scale of 0 to 14, where less than 7 represents acidity, 7 neutrality, and more than 7 alkalinity.

physical—tangible, real, and/or actual.

physically—existing, happening, occurring, acting, and/or operating in a manner that is tangible, real, and/or actual.

plurality—the state of being plural and/or more than one.

portion—a part, component, section, percentage, ratio, and/or quantity that is less than a larger whole.

power—(n) energy, a measure of energy and/or work, and/or a rate at which work is done, expressed as the amount of work per unit time and commonly measured in units such as watt and horsepower; (v) to energize, such as via applying electricity.

power conditioner—a device, machine, and/or system configured to store, convert, and/or condition electrical power.

power generator—a device, machine, and/or system configured to adaptable to produce electrical power.

ppm—parts per million.

pre-—a prefix that precedes an activity that has occurred beforehand and/or in advance.

predetermine—to determine, decide, and/or establish in advance.

preheat—to heat prior to introducing reactants into.

prepare—(v.) to make ready or suitable in advance for a particular purpose, use, event, etc.

prevent—to hinder, avert, and/or keep from occurring.

prior—before and/or preceding in time or order.

probability—a quantitative representation of a likelihood of an occurrence.

processor—a machine that provides and/or utilizes hardware, firmware, and/or software and is physically adaptable to perform, via Boolean logic operating on a plurality of logic gates that form particular physical circuits, a specific task defined by a set of machine-implementable instructions. A processor can utilize mechanical, pneumatic, hydraulic, electrical, magnetic, optical, informational, chemical, and/or biological principles, characteristics, mechanisms, components, data structures, adaptations, signals, inputs, and/or outputs to perform the task(s). In certain embodiments, a processor can act upon information by manipulating, analyzing, modifying, and/or converting it, transmitting the information for use by machine-implementable instructions and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium family of microprocessor manufactured by the Intel Corporation of Santa Clara, California. In certain embodiments, the processor can be special purpose and/or dedicated purpose device, such as an Application Specific Integrated Circuit (ASIC) or a Field Programmable Gate Array (FPGA), that has been designed to implement in its hardware and/or firmware at least a part of an embodiment disclosed herein. A processor can reside on and use the capabilities of a controller.

produce—(v.) to create and/or generate via a physical effort, manufacture, and/or make.

product—something produced by human and/or mechanical effort.

project—to calculate, estimate, or predict.

provide—to furnish, supply, give, convey, send, and/or make available.

pure—having a substantially homogeneous and/or uniform composition, not mixed, and/or substantially free of foreign substances.

range—a measure of an extent of a set of values and/or an amount and/or extent of variation and/or a defined interval characterized by a predetermined maximum value and/or a predetermined minimum value.

ratio—a relationship between two quantities expressed as a quotient of one divided by the other.

re-activate—to make active again and/or to restore the ability to function and/or the effectiveness of.

react—to cause (a substance or substances) to undergo a reaction.

reactants—substances that react in a chemical reaction.

reaction—a change and/or transformation in which a substance decomposes, combines with other substances, and/or interchanges constituents with other substances.

reaction product—something produced by a chemical reaction.

receive—to gather, take, acquire, obtain, accept, get, and/or have bestowed upon.

recommend—to suggest, praise, commend, and/or endorse.
recycle—(v.) to treat and/or process (e.g., used and/or waste materials) so as to make suitable for reuse; (adj.) suitable for reuse.
reduce—to make and/or become lesser and/or smaller.
remove—to eliminate, take away, and/or delete, and/or to move from a place or position occupied.
render—to, e.g., physically, chemically, biologically, electronically, electrically, magnetically, optically, acoustically, fluidically, and/or mechanically, etc., transform information into a form perceptible to a human as, for example, data, commands, text, graphics, audio, video, animation, and/or hyperlinks, etc., such as via a visual, audio, and/or haptic, etc., means and/or depiction, such as via a display, monitor, electric paper, ocular implant, cochlear implant, speaker, vibrator, shaker, force-feedback device, stylus, joystick, steering wheel, glove, blower, heater, cooler, pin array, tactile touchscreen, etc.
repeat—to do again and/or perform again.
repeatedly—again and again; repetitively.
request—to express a desire for and/or ask for.
result—(n.) an outcome and/or consequence of a particular action, operation, and/or course; (v.) to cause an outcome and/or consequence of a particular action, operation, and/or course.
resulting—that which is an outcome and/or consequence of a particular action, operation, and/or course.
said—when used in a system or device claim, an article indicating a subsequent claim term that has been previously introduced.
salt—a chemical compound formed by replacing all or part of the hydrogen ions of an acid with metal ions and/or electropositive radicals.
saturated—full and/or unable to hold and/or contain more.
second—a label for an element in one or more patent claims, the element other than a "first" referenced element of a similar type, but the label does not necessarily imply any type of ordering to how that "second" element or the "first" element is implemented in embodiments of the claimed subject matter.
select—to make a choice or selection from alternatives.
selectively—via choice.
server—an information device and/or a process running thereon, that is adapted to be communicatively coupled to a network and that is adapted to provide at least one service for at least one client, i.e., for at least one other information device communicatively coupled to the network and/or for at least one process running on another information device communicatively coupled to the network. One example is a file server, which has a local drive and services requests from remote clients to read, write, and/or manage files on that drive. Another example is an e-mail server, which provides at least one program that accepts, temporarily stores, relays, and/or delivers e-mail messages. Still another example is a database server, which processes database queries. Yet another example is a device server, which provides networked and/or programmable: access to, and/or monitoring, management, and/or control of, shared physical resources and/or devices, such as information devices, printers, modems, scanners, projectors, displays, lights, cameras, security equipment, proximity readers, card readers, kiosks, POS/retail equipment, phone systems, residential equipment, HVAC equipment, medical equipment, laboratory equipment, industrial equipment, machine tools, pumps, fans, motor drives, scales, programmable logic controllers, sensors, data collectors, actuators, alarms, annunciators, and/or input/output devices, etc.
set—a related plurality.
signal—(v) to communicate; (n) one or more automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc., that can encode information, such as machine-implementable instructions for activities and/or one or more letters, words, characters, symbols, signal flags, visual displays, and/or special sounds, etc., having prearranged meaning. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.
size—(n) physical dimensions, proportions, magnitude, amount, and/or extent of an entity; (v) to determine physical dimensions, proportions, magnitude, amount, and/or extent of an entity.
solid—neither liquid nor gaseous, but instead of definite shape and/or form.
source—an original and/or intermediate transmitter of electrical energy and/or a related group of such transmitters and/or a point at which something originates, springs into being, and/or from which it derives and/or is obtained.
special purpose computer—a computer and/or information device comprising a processor device having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.
special purpose processor—a processor device, having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

species—a class of individuals and/or objects grouped by virtue of their common attributes and assigned a common name; a division subordinate to a genus.

spent—used up, consumed, exhausted, and/or depleted of effectiveness.

state—a qualitative and/or quantitative description of condition.

store—to deposit, receive, place, collect, keep, retain, save, hold, accumulate, and/or retain mass and/or data.

stream—a steady current of a fluid.

substantially—to a great extent and/or degree.

sufficient—a degree and/or amount necessary to achieve a predetermined result.

sufficiently—to a degree necessary to achieve a predetermined result.

supply—to make available for use.

support—to bear the weight of, especially from below.

switch—(v) to: form, open, and/or close one or more circuits; form, complete, and/or break an electrical and/or informational path; select a path and/or circuit from a plurality of available paths and/or circuits; and/or establish a connection between disparate transmission path segments in a network (or between networks); (n) a physical device, such as a mechanical, electrical, and/or electronic device, that is adapted to switch.

synthesis gas—a combustible mixture of hydrogen and carbon monoxide, in various ratios, the mixture often containing some carbon dioxide and/or methane, and often used as a fuel.

synthetic hydrocarbons—one or more manmade organic compounds that each comprises only hydrogen and carbon or only hydrogen, carbon, and oxygen (and thus such compounds include synthetic oxygenated hydrocarbons).

system—a collection of mechanisms, devices, machines, articles of manufacture, processes, data, and/or instructions, the collection designed to perform one or more specific, practical, concrete, tangible, and/or useful functions.

that—used as the subject or object of a relative clause.

thermal decomposer—a device, machine, and/or system configured to cause thermal decomposition.

thermal decomposition—a process and/or chemical reaction via which heat is applied to simplify and/or break the chemical bonds of a single chemical entity (normal molecule, reaction intermediate, etc.) into two or more fragments and/or products.

thermal—pertaining to temperature.

through—across, among, between, and/or in one side and out the opposite and/or another side of.

to—a preposition expressing purpose.

transform—to change in measurable: form, appearance, nature, and/or character.

transmit—to send as a signal, provide, furnish, and/or supply.

treatment—an act, manner, or method of handling and/or dealing with someone and/or something.

upon—immediately or very soon after; and/or on the occasion of.

use—to utilize, apply, harness, exploit, and/or put into service.

user interface-any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

via—by way of, with, and/or utilizing.

volume—the amount of space occupied by a three dimensional object or a region of space measured in cubic units.

water—a transparent, odorless, tasteless liquid containing approximately 11.188 percent hydrogen and approximately 88.812 percent oxygen, by weight, characterized by the chemical formula $H_2O$, and, at standard pressure (approximately 14.7 psia), freezing at approximately 32° F. or 0° C. and boiling at approximately 212° F. or 100° C.

weight—a force with which a body is attracted to Earth or another celestial body, equal to the product of the object's mass and the acceleration of gravity; and/or a factor and/or value assigned to a number in a computation, such as in determining an average, to make the number's effect on the computation reflect its importance, significance, preference, impact, etc.

when—at a time and/or during the time at which.

wherein—in regard to which; and; and/or in addition to.

with—accompanied by.

with regard to—about, regarding, relative to, and/or in relation to.

with respect to—about, regarding, relative to, and/or in relation to.

within—inside the limits of.

zone—a region and/or volume having at least one predetermined boundary.

Note

Various substantially and specifically practical and useful exemplary embodiments of the claimed subject matter are described herein, textually and/or graphically, including the best mode, if any, known to the inventor(s), for implementing the claimed subject matter by persons having ordinary skill in the art. References herein to "in one embodiment", "in an embodiment", or the like do not necessarily refer to the same embodiment.

Any of numerous possible variations (e.g., modifications, augmentations, embellishments, refinements, and/or enhancements, etc.), details (e.g., species, aspects, nuances, and/or elaborations, etc.), and/or equivalents (e.g., substitutions, replacements, combinations, and/or alternatives, etc.) of one or more embodiments described herein might become apparent upon reading this document to a person having ordinary skill in the art, relying upon his/her expertise and/or knowledge of the entirety of the art and without exercising undue experimentation. The inventor(s) expects any person having ordinary skill in the art, after obtaining authorization from the inventor(s), to implement such variations, details, and/or equivalents as appropriate, and the inventor(s) therefore intends for the claimed subject matter to be practiced other than as specifically described herein. Accordingly, as permitted by law, the claimed subject matter includes and covers all variations, details, and equivalents of that claimed subject matter. Moreover, as permitted by law, every combination of the herein described characteristics, functions, activities, substances, and/or structural elements, and all possible variations, details, and equivalents thereof, is encompassed by the claimed subject matter unless otherwise clearly indicated herein, clearly and specifically disclaimed, or otherwise clearly unsuitable, inoperable, or contradicted by context.

The use of any and all examples, or exemplary language (e.g., "such as") provided herein, is intended merely to better illuminate one or more embodiments and does not pose a limitation on the scope of any claimed subject matter unless otherwise stated. No language herein should be construed as indicating any non-claimed subject matter as essential to the practice of the claimed subject matter.

Thus, regardless of the content of any portion (e.g., title, field, background, summary, description, abstract, drawing figure, etc.) of this document, unless clearly specified to the contrary, such as via explicit definition, assertion, or argument, or clearly contradicted by context, with respect to any claim, whether of this document and/or any claim of any document claiming priority hereto, and whether originally presented or otherwise:

there is no requirement for the inclusion of any particular described characteristic, function, activity, substance, or structural element, for any particular sequence of activities, for any particular combination of substances, or for any particular interrelationship of elements;

no described characteristic, function, activity, substance, or structural element is "essential"; and within, among, and between any described embodiments:

any two or more described substances can be mixed, combined, reacted, separated, and/or segregated;

any described characteristic, function, activity, substance, component, and/or structural element, or any combination thereof, can be specifically included, duplicated, excluded, combined, reordered, reconfigured, integrated, and/or segregated;

any described interrelationship, sequence, and/or dependence between any described characteristics, functions, activities, substances, components, and/or structural elements can be omitted, changed, varied, and/or reordered;

any described activity can be performed manually, semi-automatically, and/or automatically;

any described activity can be repeated, performed by multiple entities, and/or performed in multiple jurisdictions.

The use of the terms "a", "an", "said", "the", and/or similar referents in the context of describing various embodiments (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

When any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values therebetween, such as for example, 1.1, 2.5, 3.335, 5, 6.179, 8.9999, etc., and includes all sub-ranges therebetween, such as for example, 1 to 3.65, 2.8 to 8.14, 1.93 to 9, etc., even if those specific values or specific sub-ranges are not explicitly stated.

When any phrase (i.e., one or more words) appearing in a claim is followed by a drawing element number, that drawing element number is exemplary and non-limiting on claim scope.

No claim or claim element of this document is intended to invoke 35 USC 112 (f) unless the precise phrase "means for" is followed by a gerund.

Any information in any material (e.g., a United States patent, United States patent application, book, article, web page, etc.) that has been incorporated by reference herein, is incorporated by reference herein in its entirety to its fullest enabling extent permitted by law yet only to the extent that no conflict exists between such information and the other definitions, statements, and/or drawings set forth herein. In the event of such conflict, including a conflict that would render invalid any claim herein or seeking priority hereto, then any such conflicting information in such material is specifically not incorporated by reference herein. Any specific information in any portion of any material that has been incorporated by reference herein that identifies, criticizes, or compares to any prior art is not incorporated by reference herein.

Applicant intends that each claim presented herein and at any point during the prosecution of this application, and in any application that claims priority hereto, defines a distinct patentable invention and that the scope of that invention must change commensurately if and as the scope of that claim changes during its prosecution. Thus, within this document, and during prosecution of any patent application related hereto, any reference to any claimed subject matter is intended to reference the precise language of the then-pending claimed subject matter at that particular point in time only.

Accordingly, every portion (e.g., title, field, background, summary, description, abstract, drawing figure, etc.) of this document, other than the claims themselves and any provided definitions of the phrases used therein, is to be regarded as illustrative in nature, and not as restrictive. The scope of subject matter protected by any claim of any patent that issues based on this document is defined and limited only by the precise language of that claim (and all legal equivalents thereof) and any provided definition of any phrase used in that claim, as informed by the context of this document when reasonably interpreted by a person having ordinary skill in the relevant art.

What is claimed is:

1. A system configured for converting biomass to synthetic hydrocarbons, the system comprising:
   a biomass preparer configured to:
      sort and/or change a particle size, density, and/or dryness of a received biomass provided to the biomass preparer sufficiently for a resulting prepared biomass to have, on average, dimensions between approximately 0.5 and approximately 30 centimeters, a bulk density between approximately 0.2 and approximately 0.9 kilogram/liter, and/or a dryness between 0 and approximately 30 weight percent; and
      convey and/or store sufficient prepared biomass to operate a first thermal decomposer for at least 1 hour at approximately a nameplate input flow rate of the first thermal decomposer;
   the first thermal decomposer, wherein the first thermal decomposer is configured to convert prepared biomass into synthesis gas;
   a synthesis gas cleaner configured to produce cleaned synthesis gas from synthesis gas;
   a hydrocarbon synthesizer configured to produce synthetic hydrocarbons from synthesis gas and/or hydrogen-comprising gas;
   a mass and/or heat integrator configured to add natural gas, a hydrocarbon-comprising gas, and/or the hydrogen-comprising gas to a recycle mass coproduct of the hydrocarbon synthesizer for supply to the first thermal decomposer and/or a second thermal decomposer.

2. The system of claim 1, further comprising a hydrogen generator, wherein the hydrogen generator is configured to produce the hydrogen-comprising gas through water electrolysis, hydrocarbon thermal decomposition, and/or water gas shift.

3. The system of claim 1, further comprising an electrical power conditioner configured to store sufficient electrical power selectively received from an electrical power generator and/or an external electrical power source to electrically power:
   the electrolyzer at approximately 20 percent to approximately 100 percent of an electrolyzer nameplate electrical power consumption rate for at least 0.5 hours; and/or
   the system at approximately 20 percent to approximately 100 percent of a system nameplate synthetic hydrocarbon output flow rate for at least 0.5 hours.

4. The system of claim 1, further comprising a hydrogen separator configured to separate hydrogen from non-hydrogen gases to produce the hydrogen-comprising gas.

5. The system of claim 1, wherein the mass and/or heat integrator is configured to store a sufficient quantity of the hydrogen-comprising gas to operate:
   the first thermal decomposer at approximately 20 percent to approximately 100 percent of the nameplate input flow rate of the first thermal decomposer for at least 0.5 hours;
   the second thermal decomposer at approximately 20 percent to approximately 100 percent of a nameplate input flow rate of the second thermal decomposer for at least 0.5 hours;
   a hydrogen generator at approximately 20 percent to approximately 100 percent of a nameplate production rate of the hydrogen generator for at least 0.5 hours; and/or
   the hydrocarbon synthesizer at approximately 20 percent to approximately 100 percent of a nameplate hydrocarbon output flow rate of the hydrocarbon synthesizer for at least 0.5 hours.

6. The system of claim 1, wherein the mass and/or heat integrator is configured to store a sufficient quantity of the hydrocarbon-comprising gas to operate:
   the first thermal decomposer at approximately 20 percent to approximately 100 percent of the nameplate input flow rate of the first thermal decomposer for at least 0.5 hours;
   the second thermal decomposer at approximately 20 percent to approximately 100 percent of a nameplate input flow rate of the second thermal decomposer for at least 0.5 hours;
   a hydrogen generator at approximately 20 percent to approximately 100 percent of a nameplate production rate of the hydrogen generator for at least 0.5 hours; and/or
   the hydrocarbon synthesizer at approximately 20 percent to approximately 100 percent of a nameplate hydrocarbon output flow rate of the hydrocarbon synthesizer for at least 0.5 hours.

7. The system of claim 1, further comprising the supply of air, purified oxygen, electrolyzer oxygen, and/or other oxygen-comprising gas to the first thermal decomposer and/or the second thermal decomposer.

8. The system of claim 1, wherein the mass and/or heat integrator is configured to store a sufficient quantity of an oxygen-comprising gas to operate:
   the first thermal decomposer at approximately 20 percent to approximately 100 percent of the nameplate input flow rate of the first thermal decomposer for at least 0.5 hours;
   the second thermal decomposer at approximately 20 percent to approximately 100 percent of a nameplate input flow rate of the second thermal decomposer for at least 0.5 hours; and/or a hydrogen generator at approximately 20 percent to approximately 100 percent of a nameplate production rate of the hydrogen generator for at least 0.5 hours.

9. The system of claim 1, wherein the system is configured to control a ratio of hydrogen to carbon monoxide in the synthesis gas to within a range of approximately 1.3 to approximately 3.9.

10. The system of claim 1, further comprising an electrical generator operably configured to produce electrical energy from one or more sources of thermal energy, chemical energy extractable from hydrogen-comprising gas, chemical energy extracted from hydrocarbon-comprising gas, solar energy, wind energy, and/or hydroelectric energy to power one or more components of the system.

11. The system of claim 1, wherein the mass and/or heat integrator is configured to heat the prepared biomass, the hydrogen-comprising gas, the hydrocarbon-comprising gas, an oxygen-comprising gas, a water-comprising gas, a water-comprising liquid, and/or a hydrocarbon-comprising liquid to a temperature of at least 45 degrees Celsius.

12. The system of claim 1, wherein the mass and/or heat integrator is configured to store a sufficient quantity of a hydrocarbon-comprising liquid to operate the hydrocarbon synthesizer at approximately 20 percent to approximately 100 percent of a nameplate hydrocarbon output flow rate of the hydrocarbon synthesizer for at least 0.5 hours.

13. The system of claim 1, wherein the mass and/or heat integrator is configured to heat a hydrocarbon-comprising liquid to a temperature of at least 45 degrees Celsius.

14. The system of claim 1, wherein the mass and/or heat integrator is configured to store a sufficient quantity of heat to operate:

the first thermal decomposer at approximately 20 percent to approximately 100 percent of a nameplate operational temperature of the first thermal decomposer for at least 0.5 hours;

the second thermal decomposer at approximately 20 percent to approximately 100 percent of a nameplate operational temperature of the second thermal decomposer for at least 0.5 hours;

a hydrogen separator at approximately 20 percent to approximately 100 percent of a nameplate operational temperature of the hydrogen separator for at least 0.5 hours;

a hydrogen generator at approximately 20 percent to approximately 100 percent of a nameplate operational temperature of the hydrogen generator for at least 0.5 hours; and/or the hydrocarbon synthesizer at approximately 20 percent to approximately 100 percent of a nameplate operational temperature of the hydrocarbon synthesizer for at least 0.5 hours.

15. The system of claim 1, wherein the system is configured to be at least partially controlled via an offsite controller.

* * * * *